US007732194B2

(12) United States Patent
Pellenz et al.

(10) Patent No.: US 7,732,194 B2
(45) Date of Patent: Jun. 8, 2010

(54) **CHARACTERIZATION OF THE I-*SPOM*I ENDONUCLEASE FROM FISSION YEAST**

(75) Inventors: Stefan Pellenz, De-Coblence (DE); Bernard Dujon, Gif sur Yvette (FR); Alexis Harington, Paris (FR); John Sullivan Harington, legal representative, Pretoria (ZA); Eoné de Wet, legal representative, Johannesburg (ZA); Bernd Schafer, Aachen (DE)

(73) Assignees: Institut Pasteur, Paris (FR); Centre National de la Recherche Scientifique, Paris (FR); Universite Pierre et Marie Curie (Paris VI), Paris (FR)

( * ) Notice: Subject to any disclaimer, the term of this patent is extended or adjusted under 35 U.S.C. 154(b) by 760 days.

(21) Appl. No.: 11/250,633

(22) Filed: Oct. 17, 2005

(65) Prior Publication Data

US 2006/0286656 A1    Dec. 21, 2006

Related U.S. Application Data

(63) Continuation of application No. 10/933,476, filed on Sep. 3, 2004, now abandoned, which is a continuation of application No. 10/471,723, filed as application No. PCT/EP02/03357 on Mar. 12, 2002, now abandoned.

(60) Provisional application No. 60/275,638, filed on Mar. 15, 2001.

(51) Int. Cl.
| | |
|---|---|
| *C12N 15/63* | (2006.01) |
| *C12N 15/11* | (2006.01) |
| *C07H 21/04* | (2006.01) |
| *C12N 15/85* | (2006.01) |
| *C12N 9/00* | (2006.01) |

(52) U.S. Cl. .................. 435/320.1; 536/23.1; 536/23.2; 435/325

(58) Field of Classification Search ........................ None
See application file for complete search history.

(56) References Cited

U.S. PATENT DOCUMENTS

| 5,474,896 | A | 12/1995 | Dujon et al. | |
| 5,830,729 | A | 11/1998 | Jaisser et al. | |
| 2004/0031072 | A1* | 2/2004 | La Rosa et al. | ............. 800/278 |

OTHER PUBLICATIONS

McCarroll et al, Stable insect cell cultures for recmbinant protein production. Current Opin. In Biotech. 8: 590-594, 1997.*
Wickham, Targeting Adenovirus, Gene Therapy 7: 110-114, 2000.*
Accession No. AB009363.*
Inagaki et al. Algae or Protozoa: Phylogenetic Position of Euglenophytes and Dinoflagellates as Inferred from Mitochondrial Sequences. J Mol Evol 45: 295-300, 1997.*
Capecchi, "Altering the Genome by Homologous Recombination," *Science* 244:1288-1292, 1989.

Smithies et al., "Insertion of DNA Sequences into the Human Chromosomal β-globin Locus by Homologous Recombination," *Nature* 317:230-234, 1985.
Berinstein et al., "Gene Replacement with One-Sided Homologous Recombination, " *Mol. Cell Biol.* 12:360-367, 1992.
Brenner et al., "Double-strand Gap Repair Results in Homologous Recombination in Mouse L Cells," *Proc. Natl. Acad. Sci. USA* 83:1762-1766, 1986.
Lin et al., "Repair of Double-Stranded DNA Breaks by Homologous DNA Fragments During Transfer of DNA into Mouse L Cells," *Mol. Cell Biol.* 10:113-119, 1990.
Lin et al., "Intermolecular Recombination Between DNAs Introduced into Mouse L Cells is Mediated by a Nonconservative Pathway That Leads to Crossover Products," *Mol. Cell. Biol.* 10:103-112, 1990.
Jessberger and Berg, "Repair of Deletions and Double-Strand Gaps by Homologous Recombination in a Mammalian In Vitro System," *Mol. Cell Biol.* 11:445-457, 1991.
Jacquier and Dujon, "An Intron-Encoded Protein is Active in a Gene Conversion Process That Spreads an Intron into a Mitochondrial Gene," *Cell* 41:383-394, 1985.
Plessis et al., "Site-Specific Recombination Determined by I-*Sce*I, a Mitochondrial Group I Intron-Encoded Endonuclease Expressed in the Yeast Nucleus," *Genetics* 130:451-460, 1992.
Thierry et al., "Cleavage of Yeast and Bacteriophase T7 Genomes at a Single Site Using the Rare Cutter Endonuclease I-*Sce* I," *Nucleic Acids Res.* 19:189-90, 1991.
Kilby et al., "Site-Specific Recombinases: Tools for Genome Engineering," *Reviews* 9:413-421, 1993.
Szostak et al., "The Double-Strand-Break Repair Model for Recombination," *Cell* 33:25-35, 1983.
Anglana and Bacchetti, "Construction of a Recombinant Adenovirus for Efficient Delivery of the I-*Sce*I Yeast Endonuclease to Human Cells and its Application in the In Vivo Cleavage of Chromosomes to Expose New Potential Telomeres," *Nucl. Acids Res.* 27:4276-4281, 1999.
Bellaiche et al., "I-*Sce*I Endonuclease, a New Tool for Studying DNA Double-Strand Break Repair Mechanisms in Drosophila," *Genetics* 152:1037-1044, 1999.
Choulika et al., "The Yeast I-*Sce* I Meganuclease Induces Site-Directed Chromosomal Recombination in Mammalian Cells," *CR Acad. Sci. III* 317:1013-1019, 1994.
Choulika et al., "Induction of Homologous Recombination in Mammalian Chromosomes by Using the I-*Sce*I System of *Saccharomyces cerevisiae*," *Mol. Cell Biol.* 15:1968-1973, 1994.
Cohen-Tannoudji et al., "I-*Sce*I-Induced Gene Replacement at a Natural Locus in Embryonic Stem Cells," *Mol. Cell Biol.* 18:1444-1448, 1998.
Liang and Garrard, "Targeted Linearization of DNA in Vivo," *Methods* 17:95-103, 1999.

(Continued)

*Primary Examiner*—Michele K. Joike
(74) *Attorney, Agent, or Firm*—Finnegan, Henderson, Farabow, Garrett & Dunner, L.L.P.

(57) ABSTRACT

Isolated DNAs encoding the enzyme I-SpomI and its recognition and cutting site are provided. The DNA sequences can be incorporated in cloning and expression vectors, transformed cell lines and transgenic animals. The vectors are useful in gene mapping and site-directed insertion of genes.

20 Claims, 10 Drawing Sheets

OTHER PUBLICATIONS

Machida et al., "Characterization of the Transposition Pattern of the Ac Element in *Arabidopsis thaliana* Using Endonuclease I-*Sce*I," *Proc. Natl. Acad. Sci. USA* 94:8675-8680, 1997.

Melkerson-Watson et al., "Integrated Genomic Map from Uropathogenic *Escherichia coli* J96," *Infect. Immun.* 68:5933-5942, 2000.

Mogila et al., "Expression of I-*Sce* I in Drosophilia to Induce DNA Double-Strand Breaks," *Methods Mol. Biol.* 113:439-445, 1999.

Monteilhet et al., "Purification and Characterization in the in vitro Activity of I-*Sce* I, a Novel and Highly Specific Endonuclease Encoded by a Group I Intron," *Nucl. Acids Res.* 18:1407-1413, 1990.

Nahon and Raveh, "A Tool for Enhancing Site-Specific Gene Integration in Mammalian Cells," *Adv. Exp. Med. Biol.* 451:411-414, 1998.

Neuveglise et al., "A Shuttle Mutagenesis System for Tagging Genes in the Yeast *Yarrowia lipolytica*," *Gene* 213:37-46, 1998.

Nicolas et al., "Creation and Repair of Specific DNA Double-Strand Breaks in Vivo Following Infection with Adenovirus Vectors Expressing *Saccharomyces cerevisiae* HO Endonuclease," *Virology* 266:211-224, 2000.

Perrin et al., "Asymmetrical Recognition and Activity of the I-*Sce*I Endonuclease on its Site and on Intron-Exon Junctions," *Embo J.* 12:2939-2947, 1993.

Posfai et al., "Markerless Gene Replacement in *Escherichia coli* Stimulated by a Double-Strand Break in the Chromosome," *Nucl. Acids Res.* 27:4409-4415, 1999.

Puchta, "Use of I-*Sce* I to Induce DNA Double-Strand Breaks in Nicotiana," *Methods Mol. Biol.* 113:447-451, 1999.

Rong et al., "Gene Targeting by Homologous Recombination in Drosophila," *Science* 288:2013-2018, 2000.

Thierry et al., "Cleavage of Yeast and Bacteriophage T7 Genomes at a Single Site Using the Rare Cutter Endonuclease I-*Sce* I," *Nucl. Acids Res.* 19:189-190, 1991.

Segal et al., "Endonuclease-Induced, Targeted Homologous Extrachromosomal Recombination in *Xenopus oocytes*," *Proc. Natl. Acad. Sci. USA* 92:806-810, 1995.

Kirk et al., "Species-Specific Double-Strand Break Repair and Genome Evolution in Plants," *EMBO* 19(20):5562-5566, 2000.

Fairhead and Dujon, "Consequences of Unique Double-stranded Breaks in Yeast Chromosomes: Death or Homozygosis," *Mol. Gen. Genet.* 240:170-180, 1993.

LeMouellic et al., "Targeted Replacement of the Homeobox Gene Hox-3.1 by the *Escherichia coli lacZ* in Mouse Chimeric Embryos," *Proc. Natl. Acad. Sci. USA* 87:4712-4716, 1990.

Valancius and Smithies, "Double-Strand Gap Repair in a Mammalian Gene Targeting Reaction," *Mol. Cell Biol.* 11:4389-4397, 1991.

Dujon, "Group I Introns as Mobile Genetic Elements: Facts and Mechanistic Speculations—a Review," *Gene* 82:91-114, 1989.

Lambowitz et al., "Introns as Mobile Genetic Elements," *Annu Rev. Biochem.* 62 (5):87-622, 1993.

Belfort et al., "Homing Endonucleases: Keeping the House in Order," *Nucleic Acids Res.* 25:3379-3388, 1997.

Jurica et al., "Homing Endonucleases: Structure, Function and Evolution," *Cell Mol. Life Sci.* 55:1304-1326, 1999.

Kennell et al., "Reverse Transcriptase Activity Associated with Maturase-Encoding Group II Introns in Yeast Mitochondria," *Cell*, 73:133-146, 1993.

Zimmerly et al., "A Group II Intron RNA is a Catalytic Component of a DNA Endonuclease Involved in Intron Mobility," *Cell* 83:529-538, 1995.

Guo et al., "Group II Intron Endonucleases Use Both RNA and Protein Subunits for Recognition of Specific Sequences in Double-Stranded DNA," *Embo J.* 16:6835-6848, 1997.

Kane et al., "Protein Splicing Converts the Yeast TFP1 Gene Product to the 69-kD Subunit of the Vacuolar $H^+$-Adenosine Triphosphatase," *Science* 250:651-657, 1990.

Shub et al., "Protein Introns: A New Home for Endonucleases," *Cell* 71:183-186, 1992.

Dalgaard et al., "Statistical Modeling and Analysis of the LAGLIDADG Family of Site-Specific Endonucleases and Identification of an Intein that Encodes a Site-Specific Endonuclease of the HNH Family," *Nucleic Acids Res.* 25;4626-4638, 1997.

Pietrokovski, "Modular Organization of Inteins and C-Terminal Autocatalytic Domains," *Protein Sci.* 7:64-71, 1998.

Perler, "Protein Splicing of Inteins and Hedgehog Autoproteolysis: Structure, Function, and Evolution," *Cell*, 92:1-4, 1998.

Derbyshire et al. "Genetic Definition of a Protein-Splicing Domain: Functional Mini-Inteins Support Structure Predictions and a Model for Intein Evolution,", *Proc. Natl. Acad. Sci. USA* 94:11466-11471, 1997.

Hu et al., "Probing the Structure of the PI-*Sce*I-DNA Complex by Affinity Cleavage and Affinity Photocross-Linking," *J. Biol. Chem.* 275:2705-2712, 2000.

Ichiyanagi et al., "Crystal Structure of an Archaeal Intein-Encoded Homing Endonuclease PI-*Pfu*I," *J. Mol. Biol.* 300:889-901, 2000.

Colleaux et al., "Recognition and Cleavage Site of the Intron-Encoded *Omega* Transposase," *Proc. Natl. Acad. Sci. USA* 85:6022-6026, 1988.

Thompson et al., "Cleavage and Recognition Pattern of a Double-Strand-Specific Endonuclease (I-*Cre*I) Encoded by the Chloroplast 23S rRNA Intron of *Chlamydomonas reinhardtii*," *Gene*, 119:247-251, 1992.

Dalgaard et al., "Purification and Characterization of Two Forms of I-*Dmo*I, a Thermophilic Site-Specific Endonuclease Encoded by an Archaeal Intron," *J. Biol. Chem* 269:28885-28892, 1994.

Wernette et al., "Purification of a Site-Specific Endonuclease, I-*Sce* II, Encoded by Intron 4α of the Mitochondrial *cox*I Gene of *Saccharomyces cerevisiae*," *J. Biol. Chem.* 265:18976-18982, 1990.

Dalgaard et al., "A Site-Specific Endonuclease Encoded by a Typical Archaeal Intron," *Proc. Natl. Acad. Sci. USA* 90:5414-5417, 1993.

Heath et al., "The Structure of I-*Cre*I, a Group I Intron-Encoded Homing Endonuclease," *Nat. Struct. Biol.* 4:468-476, 1997.

Duan et al., "Crystal Structure of PI-*Sce*I, a Homing Endonuclease with Protein Splicing Activity," *Cell*, 89:555-564, 1997.

Silva et al., "Crystal Structure of the Thermostable Archaeal Intron-Encoded Endonuclease I-*Dmo*I," *J. Mol. Biol.* 286:1123-1136, 1999.

Flick et al., "DNA Binding and Cleavage by the Nuclear Intron-Encoded Homing Endonuclease I-*Ppo*I," *Nature* 394:96-101, 1998.

Wittmayer et al., "Substrate Binding and Turnover by the Highly Specific I-*Ppo*I Endonuclease," *Biochemistry* 35:1076-1083, 1996.

Pingoud et al., "Recognition and Cleavage of DNA by Type-II Endonucleases," *Eur. J. Biochem.* 246:1-22, 1997.

Kuhlmann et al., "Structural Parsimony in Endonuclease Active Sites: Should the Number of Homing Endonuclease Families be Redefined?," *FEBS Lett.* 463:1-2, 1999.

Wernette, "Structure and Activity of the Mitochondrial Intron-Encoded Endonuclease, I-*Sce*IV," *Biochem Biophys. Res. Commun.* 248:127-133, 1998.

Marshall et al., "Cleavage Pattern of the Homing Endonuclease Encoded by the Fifth Intron in the Chloroplast Large Subunit rRNA-Encoding Gene of *Chlamydomonas eugametos*," *Gene* 104:241-245, 1991.

Lykke-Andersen et al., "Protein Footprinting Approach to Mapping DNA Binding Sites of Two Archaeal Homing Enzymes: Evidence for a Two-Domain Protein Structure," *Nucleic Acids Res.* 24:3982-3989, 1996.

Lazowska et al., "Sequence of Introns and Flanking Exons in Wild-Type and *box*3 Mutants of Cytochrome b Reveals an Interlaced Splicing Protein Coded by an Intron," *Cell* 22:333-348, 1980.

De La Salle et al., "Critical Sequences within Mitochondrial Introns: Pleiotropic mRNA Maturase and Cis-Dominant Signals of the *box* Intron controlling Reductase and Oxidase," *Cell* 28:721-732, 1982.

Lambowitz et al., "Involvement of Aminoacyl-tRNA Synthetases and Other Proteins in Group I and Group II Intron Splicing," *Trends Biochem. Sci.* 15:440-444, 1990.

Weeks et al., "Assembly of a Ribonucleoprotein Catalyst by Tertiary Structure Capture," *Science* 271:345-348, 1996.

Dujardin et al., "Single Base Substitution in an Intron of Oxidase Gene Compensates Splicing Defects of the Cytochrome *b* Gene," *Nature* 298:628-632, 1982.

Wenzlau et al., "A Latent Intron-Encoded Maturase is Also an Endonuclease Needed for Intron Mobility," *Cell* 56:421-430, 1989.

Szczepanek et al. "Critical Bse Substitutions that Affect the Splicing and/or Homing Activities of the Group I Intron bi2 of Yeast Mitochondria," *Mol Gen. Genet.* 264:137-144, 2000.

Ho et al., "A Protein Encoded by a Group I Intron in *Aspergillus nidulans* Directly Assists RNA Splicing and is a DNA Endonuclease," *Proc. Natl. Acad. Sci. USA* 94:8994-8999, 1997.

Ho et al., "The Maturase Encoded by a Group I Intron from *Aspergillus nidulans* Stabilizes RNA Tertiary Structure and Promotes Rapid Splicing," *J. Mol. Biol.* 292:987-1001, 1999.

Lazowska et al., "Two Homologous Mitochondrial Introns from Closely Related *Saccharomyces* Species Differ by Only a Few Amino Acid Replacements in Their Open Reading Frames: One is Mobile, the Other is Not," *C.R. Acad. Sci. III* 315:37-41, 1992.

Szczepanek et al., "Replacement of Two Non-Adjacent Amino Acids in the *S. cerevisiae* bi2 Intron-Encoded RNA Maturase is Sufficient to Gain a Homing-Endonuclease Activity," *EMBO J.* 15:3758-3767, 1996.

Monteilhet et al., "Purification and Characterization of the DNA Cleavage and Recognition Site of I-*Sca*I Mitochondrial Group I Intron Encoded Endonuclease Produced in *Escherichia coli*," *Nucleic Acids Res.* 28:1245-1251, 2000.

Schafer et al., "The Mitochondrial Genome of Fission Yeast: Inability of all Introns to Splice Autocatalytically, and Construction and Characterization of an Intronless Genome," *Mol. Gen. Genet.* 225:158-167, 1991.

Lang, et al., "Sequence of the Mitochondrial DNA, Arrangement of Genes and Processing of Their Transcripts in *Schizosaccharomyces pombe*," *Mitochondria*, Walter de Gruyter, Berlin, NY, 1983.

Lang, "The Mitochondrian Genome of the Fission Yeast *Schizosaccharomyces pombe*: Highly Homologous Introns are Inserted at the Same Position of the Otherwise Less Conserved *cox*1 genes in *Schizosaccharomyces pombe* and *Aspergillus nidulans*," *EMBO J.* 3:2129-2136, 1984.

Schafer et al., "A Mitochondrial Group-I Intron in Fission Yeast Encodes a Maturase and is Mobile in Crosses," *Curr. Genet.* 25:336-341, 1994.

Schafer et al., "The Mobile Introns in Fission Yeast Mitochondria: A Short Review and New Data," in *Eukaryotism and Symbiosis: Intertaxonic combination versus symbiotic adaptation*, Schenk et al. (eds.), Springer-Verlag, Berlin, Geidelbert, New York, pp. 139-144, 1997.

Merlos-Lange et al., "DNA Splicing of Mitochondrial Group I and II Introns in *Schizosaccharomyces pombe*," *Mol. Gen. Genet.* 206:273-278, 1987.

Wang et al., "Purification, Biochemical Characterization and Protein-DNA Interactions of the I-*Cre*I Endonuclease Produced in *Escherichia coli*," *Nucleic Acids Res.* 25:3767-3776, 1997.

Muscarella et al., "Characterization of I-*Ppo*, an Intron-Encoded Endonuclease that Mediates Homing of a Group I Intron in the Ribosomal DNA of *Physarum polycephalum*," *Mol. Cell Biol.* 10:3386-3396, 1990.

Schapira et al., "I-*Sce*III an Intron-Encoded DNA Endonuclease from Yeast Mitochondria. Asymmetrical DNA Binding Properties and Cleavage Reaction," *Nucleic Acids Res.* 21:3683-3689, 1993.

Guo et al., "The Mobile Group I Intron 3α of the Yeast Mitochondrial *COX*I Gene Encodes a 35-kDA Processed Protein That is an Endonuclease but Not a Maturase," *J. Biol. Chem.* 270:15563-15570, 1995.

Perea et al., "I-*Sce* III: a Novel Group I Intron-Encoded Endonuclease from the Yeast Mitochondria," *Nucleic Acids Res.* 21:358, 1993.

Cote et al., "The Single Group-I Intron in the Chloroplast *rrnL* of *Chlamydomonas humicola* Encodes a Site-Specific DNA Endonuclease (I-*Chu*I)," *Gene* 129:69-76, 1993.

Turmel et al., "The SIte-Specific DNA Endonuclease Encoded by a Group I Intron in the *Chlamydomonas pallidostigmatica* Chloroplast Small Subunit of rRNA Gene Introduces a Single-Stand Break at Low Concentrations of $Mg^{2+}$," *Nucleic Acids Res.* 23:2519-2525, 1995.

Lykke-Andersen et al., "DNA Substrate Specificity and Cleavage Kinetics of an Archaeal Homing-Type Endonuclease from *Pyrobaculum organotrophum*," *Nucleic Acids Res.* 22:4583-4590, 1994.

Gimble et al., "Homing of a NDA Endonuclease Gene by Meiotic Gene Conversion in *Saccharomyces cerevisiae*," *Nature* 357:301-306, 1992.

Saves et al., "The *Thy* Pol-2 Intein of *Thermococcus hydrothermalis* in an Isoschizomer of PI-*Tli*I and PI-*Tfu*II Endonucleases," *Nucleic Acids Res.* 28:4391-4396, 2000.

Perler et al., "Intervening Sequences in an Archaea DNA Polymrease Gene," *Proc. Natl. Acad. Sci. USA* 89:5577-5581, 1992.

Saves, "Inteins of *Thermococcus fumicolans* DNA Polymerase are Endonucleases with Distinct Enzymatic Behaviors," *J. Biol. Chem.* 275:2335-2341, 2000.

Kostriken et al., "A Site-Specific Endonuclease Essential for Mating-Type Switching in *Saccharomyces cerevisiae*," *Cell* 35:167-174, 1983.

Argast et al., "I-*Ppo*I and I-*Cre*I Homing Site Sequence Degeneracy Determined by Random Mutagenesis and Sequential in Vitro Enrichment," *J. Mol. Biol.* 280:345-353, 1998.

Jurica et al., "DNA Recognition and Cleavage by the LAGLIDADG Homing Endonuclease I-*Cre*I," *Mol. Cell* 2:469-476, 1998.

Lambowitz, "Infectious Introns," *Cell* 56:323-326, 1989.

Belfort, "Phage T4 Introns: Self-Splicing and Mobility," *Annu. Rev. Genet.* 24:363-385, 1990.

Loizos et al., "Evolution of Mobile Group I Introns: Recognition of Intron Sequences by an Intron-Encoded Endonuclease," *Proc. Natl. Acad. Sci. USA* 91:11983-11987, 1994.

Bell-Pedersen et al., "Intron Mobility in Phase T4 is Dependent Upon a Distinctive Class of Endonucleases and Independent of DNA Sequences Encoding the Intron Core: Mechanistic and Evolutionary Implications," *Nucleic Acids Res.* 18:3763-3770, 1990.

Michel et al., "Modelling of the Three-Dimensional Architecture of Group I Catalytic Introns Based on Comparative Sequence Analysis," *J. Mol. Biol.* 216:585-610, 1990.

Rochaix et al., "The Chloroplast Ribosomal Intron of *Chlamydomonas reinhardii* Codes for a Polypeptide Related to Mitochondrial Maturases," *Nucleic Acids Res.* 13:975-984, 1985.

Ogawa et al., "A Site-Specific DNA Endonuclease Specified by One of Two ORDs Encoded by a Group I Intron in *Dictyostelium discoideum* Mityochondrial DNA," *Gene* 191:115-121, 1997.

Henke et al., "Maturase and Endonuclease Functions Depend on Separate Conserved Domains of the Bifunctional Protein Encoded by the Group I Intron al4α of Yeast Mitochondrial DNA," *EMBO J.* 14:5094-5099, 1995.

Manna et al., "The Mitochondrial Genome of *Schizosaccharomyces pombe* Stimulation of Intra-Chromosomal Recombination in *Escherichia coli* by the Gene Product of the First *cox*1 Intron," *Curr. Genet.*, 19(4):295-300, 1991.

Lang et al., "*Schizosaccharomyces pombe* Complete Mitochondrial Genome," Database Accession No. X54421, XP002224054, Nov. 1990.

Schaefer et al., "*S. pombe* DNA for cox1/1", Database Accession No. X57664, XP002224055, Feb. 1992.

Lang, "Hypothetical cox1 Intron-1 45.6 kDa Protein," Database Accession No. P22191, XP002224056, Aug. 1991.

Pellenz et al., "Characterization of the I-spom I Endonuclease from Fission Yeast: Insights into the Evolution of a Group I Intron-encoded Homing Endonuclease," *J. Molecular Evolution*, 55(3):302-13, (2002).

Dujon et al., "Characterization of the I-spom I Endonuclease from Fission Yeast," Specification of U.S. Appl. No. 10/622,830, filed Jul. 21, 2003.

International Search Report, PCT/EP02/03357, Jan. 17, 2003.

Database EMBL [Online] Feb. 10, 1992 Schaefer B. et al.: '*S. pombe* DNA for cox1/1' Database Accession No. X57664.

Database SWISSPROT [Online] Aug. 1, 1991 Lang BF: 'Hypothetical cox1 intron-1 45.6 kDa protein' Database accession No. P22191.

Database EMBL [Online] Nov. 28, 1990 Lang BF: '*Schizosaccharomyces pombe* complete mitochondrial genome' Database accession No. X54421.

Current Genetics, vol. 19, No. 4, 1991, pp. 295-300, ISSN: 0172-8083.

PCT International Preliminary Examination Report, International Application No. PCT/EP02/03357, dated Aug. 6, 2003.

* cited by examiner

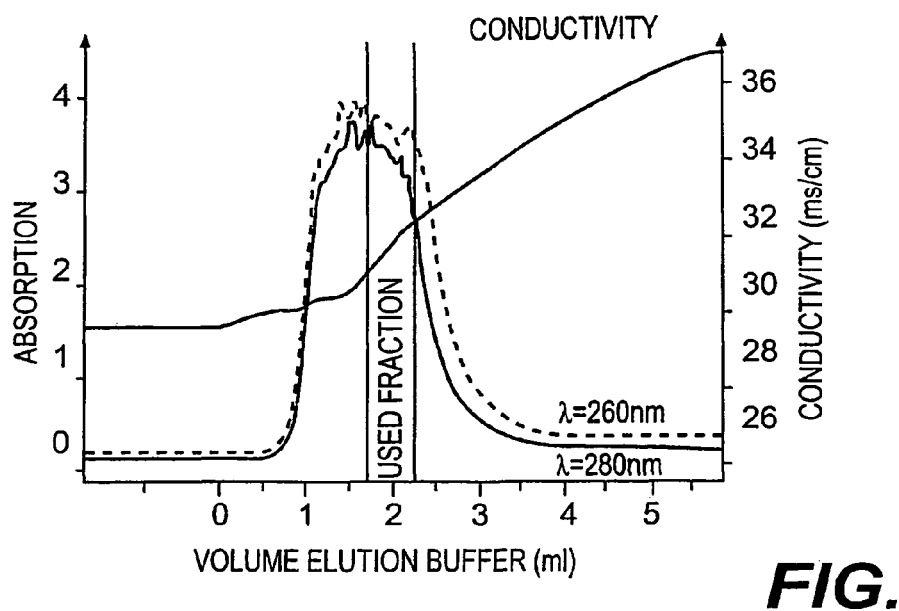
FIG. 2A
FIG. 2B
FIG. 2C

ATGAACTCTTGGTGGACTTATGTTAATAGATGGATATATTCTCAACTAATGCTAAGGATAT
TGCCATACTATATTATTATTCGGATTGGTATCTGGGATAATTGGATCTGTATTCTCTT
TTATAATTAGAATGGAACTATCAGCTCCAGGATCTCAATTCCTTTCTGGAAATGGTCAA
TTATACAATGTTGCAATCTCAGCACACATGGTATACTTATGATTTTTCTTCATTATTCCT
GCTTTATTTGGTGCATTTGGTAATTATTTAGTACCTCTTATGATAGGTGCTCTAATGT
TGCTTACCCTAGAGAGTACATTAACAGAAGAAGGACCTGGTGGTTGGACGGTTTAAAGCC
TATTAATTTCTGCATTAACAGAAGAAGGACCTGGTGGTTGGACGGTTTAAAGCC
GCAGACAAAATTGTCTGAAAACTCTTCGATGCGAAAAGTCCTCTACTCGAAGTA
ATTACTCAGTTAATTTATTTTTAACTAGTAAAAAGATTACTAACTTGGGGAAAATTCGC
CTGGTTAAATCCATCAGAGACTCGTTCTATCAGAAAATATTTATGTTCTTT
TTGGTTTATAGAACAACATACTCTTTCGAGTGTGTTAATGAAGAGTTCTTATTTAA
TAAATTTTTAATAGACATCCTTTACAAGGGTAAGGATTTACTAGGTGTGTTCATCTTCACC
ATCAAAATTCTCTTTTACTCAATGGTTAGTAGGATTTACTGATGGTGATGGTTGTTTTA
GTATTTCAAAACAAAATAAAATAGAATGGCAAAATAAATGGTCTCTTACTTTTAAATTAA
CACAAAATCTTATAATTTATATAGTAAATCAGTAATACAGTAATATAGATTAGGTATTGGTT
CACTTTATAAAGAATCTTCAACTAATACAGTCCCTCTTTAACTAGATTAAGAAGAGAGCAT
CTTAAAAGATTATAGATATTTGATCAATTCCCTCTTTAGAGGACGCTAAATCTAAATTCTTTTGAA
TATTATTGTTTAAAAAAGCATTCTTAATTTAACTAGAAGATCAGAATAGACAATATTCTCC
AAAAATAGTAAACTAGAAGAGATATTTAACAAAGTCTTGGATTTATTGAAGCAGAAG
AGTTAATTTAGAAAAATTACTACAAAAGCCCTGTAAGAATAATTCATGGGTTGAGATTACT
GGAGCTTTATTGAACAACCCCTACTGCTTATTTCATCATGGGTTGAGATTACT
CAAAATTATGAACAACCCCTACTTGCTCAGAGTTCAGAGTTCCTATTTAATTCTCAAAT
CTCACCAAAATAAAATCAAAAAAAATTCCTAATTACAAATTATTCCTTATCAACTAG
TTCAAAAGAAAGAATGTTAAAATTGGTCTAGATCTTTTACGTAAAATTATAATTTGAACAGCT
ATCATTAGAGCTAGAGATTAATTAGAGAAAATTAAAAATAAATTTCCCGAGGATCACAAC
ATCCAAAGGATAAATAA
(SEQ ID NO: 8)

FIG. 7

ATGAATAAATTTTTAATAGACATCCTTTTACAAGGGTAAAAAGCTGTTTTCATCATCT
TCACCATCAAAAATTCTCTTTTACTCAAGGTTAGTAGGATTACTGATGGTGATGGTTG
TTTAGTATTTCAAAACAAAATAAATGGCAAAAATAAATGGTCTCTTACTTTTAA
ATTAACACAAAATCTTTATATTATAGAATTTATATTTATTAAGAGAAATTAGGTATT
GGTTCACTTATAAAGAATCTTCAACTAATACAGTAATATATAAGAAGAGA
GCATCTTAAAAAGATTATAGATATTTTGATCAATTCCCTCTTTAACTAAAAATATTG
GGATTATTATTGTTTAAAAAGCATTCTTAATTTTAGAGGACGCTAATCTAAATTCTTT
TGAAAAAAGTAGTAAACTAGAGAGATCAGAATAATATTAACAAAGTCTTTAAAACAAT
ATTCTCCAGTTAATTTAGAAAATATTTACAAAAGTCTTGGTTAATTGGATTTATTGAAG
CAGAAGGGAGCTTTATTTACTACAACAACCCCTGCTCAGATTTCAGAGTTCATGGTTTGA
GATTACTCAAATCTCACCAAAAATCAAAAATAATCCTTAATTACAAATTATTCCTTAT
CAACTAGTTCAAAAGAAGAATGTTATTTCTTTCATCTATTTGAAAATTGTTTTAAAG
GAGTAAAAATCATTAGAATTTAAAATTTGGTCTAGATCTTTACGTAAAAATTATAATTTTG
AACAGCTTTTAAGAGCTAGAGATTTAATTAGAGAAAATTAAAATAAAAATAAATATTCCCGAGGA
TCAACAACATCCAAAGGATAAATAA
(SEQ ID NO: 9)

FIG. 8 acctggtggtGGTTGGACGGTATATCCACCactatcaagt
(SEQ ID NO: 10)

FIG. 9

MNSWWTYVNRWMFSTNAKDIAMTYLLFGLVSGMIGSVFSFMIRMETSAPGSQFTSGNG
QLYNVAISAHGMTMIFFIIPALFGAFGNYLVPTMMGAPDVAYPRVNNFTFWLTPPATMTL
LISALTEEGPGGGWTVLKPQTKLSENSSRCEKVTYSEVITQLIYFLTSKKITNLGKIRTVKSI
RDSFTSQLENILCFFLVYRTTYSFGVCLMKRFLFNKFFNRHPFTRVKSCFSSSSPSKFSFT
QWLVGFTDGDGCFSISKQKMKNGKNKWSTTFKLTQNTYNYRILYFIKRNLGISTYKESS
TNTVMYRLRRREHTKKIMDIFDQFPTLTKKYWDYLFKKAFLIEAEGSFYLTQKSPVNLEKYLTKSWLIGFIEAEGS
RMEKKSLKQYSPVNLEKYLTKSWLIGFIEAEGSFYLTQKSPVRMHGFEITQNYEQPTTAQ
ISEFTENSQISPKMKSKKNSLITNYSLSTSSKERMLFTSSYFENCFKGVKSLEFKIWSRSLR
KNYNFEQTLRARDLIRKLKNKYSRGSQHPKDK
(SEQ ID NO: 11)

FIG. 10

MNKFFNRHPFTRVKSCFSSSSPSKFSFTQWLVGFTDGDGCFSISKQKMKNGKNKWSTT
FKLTQNTYNYRILYFIKRNLGISTYKESSTNTVMYRLRRREHTKKIMDIFDQFPTLTKKYW
DYLFKKAFLIEDANTNSFEKNSKTEEIRMEKKSLKQYSPVNLEKYLTKSWLIGFIEAEGS
FYLTQKSPVRMHGFEITQNYEQPTTAQISEFTENSQISPKMKSKKNSLITNYSLSTSSKER
MLFTSSYFENCFKGVKSLEFKIWSRSLRKNYNFEQTLRARDLIRKLKNKYSRGSQHPKDK
(SEQ ID NO: 12)

FIG. 11

CHARACTERIZATION OF THE I-*SPOMI* ENDONUCLEASE FROM FISSION YEAST

CROSS REFERENCE TO RELATED APPLICATIONS

This application is a continuation of application Ser. No. 10/933,476, filed Sep. 3, 2004, now abandoned which is a continuation of application Ser. No. 10/471,723, filed Sep. 15, 2003, now abandoned which is a National Phase Application based on PCT/EP02/03357, filed on Mar. 12, 2002, and claims the benefit of U.S. Provisional Application No. 60/275,638, filed on Mar. 15, 2001, all of which are incorporated herein by reference.

FIELD OF THE INVENTION

This invention relates to a nucleotide sequence that encodes the restriction endonuclease I-SpomI and a nucleotide sequence that corresponds to an I-SpomI restriction site. This invention also relates to vectors containing the nucleotide sequences, cells transformed with the vectors, transgenic organisms based on the vectors, and cell lines derived from cells in the organisms. This invention also relates to the use of I-SpomI for mapping eukaryotic genomes and for in vivo site directed genetic recombination.

BACKGROUND OF THE INVENTION

The ability to introduce genes into the germ line of organisms, for example mammals, is of great interest in biology. The propensity of mammalian cells to take up exogenously added DNA and to express genes included in the DNA has been known for many years. The results of gene manipulation are inherited by the offspring of these animals. All cells of these offspring inherit the introduced gene as part of their genetic make-up. Such animals are said to be transgenic.

Transgenic mammals have provided a means for studying gene regulation during embryogenesis and in differentiation, for studying the action of genes, and for studying the intricate interaction of cells in the immune system. The whole animal is the ultimate assay system for manipulated genes, which direct complex biological processes.

Transgenic animals can provide a general assay for functionally dissecting DNA sequences responsible for tissue specific or developmental regulation of a variety of genes. In addition, transgenic animals provide useful vehicles for expressing recombinant proteins and for generating precise animal models of human genetic disorders.

For a general discussion of gene cloning and expression in animals and animal cells, see Sambrook et al., *Molecular Cloning: A Laboratory Manual*, 3 ed., Cold Spring Harbor Laboratory Press, 2001, and Green et al., *Genome Analysis: A Laboratory Manual* Cold Spring Harbor Laboratory Press, 1997.

Transgenic lines, which have a predisposition to specific diseases and genetic disorders, are of great value in the investigation of the events leading to these states. It is well known that the efficacy of treatment of a genetic disorder may be dependent on identification of the gene defect that is the primary cause of the disorder. The discovery of effective treatments can be expedited by providing an animal model that will lead to the disease or disorder, which will enable the study of the efficacy, safety, and mode of action of treatment protocols, such as genetic recombination.

Homologous recombination (HR) between chromosomal and exogenous DNA is at the basis of methods for introducing genetic changes into the genome (Capecchi, *Science* 244: 1288-1292, 1989; Smithies et al., *Nature* 317: 230-234, 1985). Parameters of the recombination mechanism have been determined by studying plasmid sequences introduced into cells (Bernstein, et al., *Mol. Cell Biol.* 12: 360-367, 1992; Brenner et al., *Proc. Natl. Acad. Sci. USA.* 83: 1762-1766, 1986; Lin et al., *Mol. Cell Biol.* 10:113-119, 1990; Lin et al., *Mol. Cell Biol.* 10: 103-112, 1990) and in in vitro system (Jessberger and Berg, *Mol. Cell Biol.* 11: 445-457, 1991). HR is promoted by double-strand breaks in DNA Among endonucleases, the *Saccharomyces cerevisiae* mitochondrial endonuclease I-Sce I (Jacquier and Dujon, *Cell* 41: 383-394, 1985) has characteristics, which can be exploited as a tool for cleaving a specific chromosomal target and, therefore, manipulating the chromosome in living organisms (U.S. Pat. No. 5,474,896). I-Sce I protein is an endonuclease responsible for intron homing in mitochondria of yeast, a non-reciprocal mechanism by which a predetermined sequence becomes inserted at a predetermined site. It has been established that endonuclease I-Sce I can catalyze recombination in the nucleus of yeast by initiating a double-strand break (Plessis et al, *Genetics* 130: 451-460, 1992). The recognition site of endonuclease I-Sce I is 18 bp long, therefore, the I-Sce I protein is a very rare cutting restriction endonuclease in genomes (Thierry et al., *Nucleic Acids Res.* 19: 189-90, 1991). In addition, as the I-Sce I protein is not a recombinase, its potential for chromosome engineering is larger than that of systems with target site requirements on both host and donor molecules (Kilby et al., *Reviews* 9: 413-421, 1993).

The yeast I-Sce I endonuclease can efficiently induce double-strand breaks in a chromosomal target in mammalian cells and the breaks can be repaired using a donor molecule that shares homology with the regions flanking the break resulting in site-specific recombination, gene replacement, or insertion (U.S. Pat. No. 5,474,896). The enzyme catalyzes recombination at a high efficiency. This demonstrates that recombination between chromosomal DNA and exogenous DNA can occur in mammalian cells by the double-stand break repair pathway (Szostak et al., *Cell* 33: 25-35, 1983).

I-SceI has been used for many different applications. Such applications have involved the study of double-stranded breaks, the investigation of chromosome structure, the study of transposition, inducing gene replacement in mammalian and bacterial cells, gene targeting by homologous recombination in *Drosophila*, and the production of chromosomal breaks in plants. Anglana and Bacchetti, *Nucl. Acids Res.* 27: 4276-4281, 1999; Bellaiche et al., *Genetics* 152: 1037-1044, 1999; Choulika et al., *CR Acad. Sci. III* 317: 1013-1019, 1994; Choulikia et al., *Mol. Cell Biol.* 15: 1968-1973, 1994; Cohen-Tannoudji et al., *Mol. Cell Biol.* 18: 1444-1448, 1998; Liang et al. and Garrard, *Methods* 17: 95-103, 1999; Machida et al., *Proc. Natl. Acad. Sci. USA* 94: 8675-8680, 1997; Melkerson-Watson et al., Infect. Immun. 69: 5933-5942, 2000; Mogila et al., *Methods Mol. Biol.* 113: 439-445, 1999; Monteilhet et al., *Nucl. Acids Res.* 18: 1407-1413; Nahon and Raveh, *Adv. Exp. Med. Biol.* 451: 411-414, 1998; Neuveglise et al., *Gene* 213: 37-46, 1998; Nicolas et al., *Virology* 266: 211-224, 2000; Perrin et al., Embo J. 12: 2939-2947, 1993; Posfai et al., *Nucl. Acids Res.* 27: 4409-4415; Puchta, *Methods Mol. Biol.* 113: 447-451, 1999; Rong et al., *Science* 288: 2013-2018; Thierry et al., *Nucl Acids Res.* 19: 189-190; and A. Plessis et al., *Genetics* 130: 451-460, 1992.

Group I introns are widespread in many evolutionary phylums because of their efficient propagation mechanism. Some of them encode homing endonucleases, which recognize the intron insertion site in an intronless cognate DNA-sequence and introduce double-strand breaks in the DNA near that site. Afterwards, the intron-containing gene acts as template for the repair of the cleaved recipient allele, in a gene conversion process, which leads to the duplication of the intervening sequence (1-4). In contrast to the group I intron homing, group II intron mobility is based on a retrohoming mechanism promoted by the intron encoded protein bound to the intron lariat, forming a ribonucleoprotein (RNP) particle. The RNP particle results in intron integration into the DNA target site by reversed splicing and reverse transcription of the intron RNA (5). In addition to this, the protein component is endowed with endonucleolytic activity, which cuts the antisense strand. After the RNA is positioned on the DNA it integrates into the sense strand before the antisense strand is cleaved by the protein part (6). Thus, both intronic RNA and protein component of the RNP particle are involved in the recognition of the intron target site. The latter element is also essential for DNA-unwinding (7). But not only group I- and group II-introns undergo homing. Some DNA sequences encoding inteins, polypeptides that are postranslationally removed, propagate in the same manner described for group I-introns. Inteins contain endonucleases of the LAGLIDADG (SEQ ID NO: 17) family or of the H-N-H family (3,8-12). It is likely, that these enzymes have evolved by invasion of an endonuclease gene into a preexisting intein carrying the protein splicing activity (13). Structural examinations on the crystals of the intein endonucleases PI-SceI and PI-PfuI strongly suggest that, in contrast to group I intron endonucleases, they use an additional DNA-binding domain to enhance their specificity. In PI-SceI, the DNA recognition region (DRR) establishes specific substrate contacts about two helical turns distant from the cleavage site (14), while in PI-PfuI the stirrup domain fulfills the same purpose (15).

LAGLIDADG (SEQ ID NO: 17) homing endonucleases produce 4bp 3'-OH overhangs near the intron insertion site (16-18). Conditions for optimal activity depend on the enzyme. For example, I-SceII prepared out of mitochondria (19) prefers temperatures around 30° C. and neutral pH whereas I-DmoI (18,20) prefers temperatures around 70° C. and alkaline pH- values. Unlike bacterial Type II restriction enzymes, homing endonucleases must have a very high recognition sequence specificity to exclude noxious effects on the host genome because no cognate modification system exists. Therefore, their recognition sites are much longer (14-30bp, up to 40bp for some intein encoded endonucleases). As it has been shown for the crystallized enzymes I-CreI (21), PI-SceI (22), I-DmoI (23) and the His-Cys box homing endonuclease I-PpoI (24), intron encoded homing endonucleases rely on β-sheets to make their contacts with the DNA major groove. Hence their profile is very flat and they cover a wide area on the DNA (23,25), whereas the globular restriction endonucleases (26) usually interact via side chains from their α-helices with the target sequence (4). Known homing endonucleases were classified into four families depending on the occurrence of consensus motifs (LAGLIDADG (SEQ ID NO: 17), GIY-YIG, H-N-H and His-Cys box). The latter two groups are now classified on a structural basis into a single group, the ββα-Me group (27). Members of the bacterial type II restriction enzymes are more divergent in contrast to this. The endonucleases belonging to the LAGLIDADG (SEQ ID NO: 17) protein family are the most common representatives. The main characteristic of this class is a dodecapeptide motif, which occurs one or two times in the protein.

Endonucleases with one motif bind their substrate as homodimers, whereas the enzymes with two LAGLIDADG (SEQ ID NO: 17) motifs tend to act as monomers. Exceptions are I-SceII, encoded by intron aI4α of the cox1 gene in *S. cerevisiae*, and I-SceIV from intron cox1I5α of the same organism. I-SceII possesses two dodecapeptide motifs but is active as a homodimer (19). I-SceIV acts as a heterodimer (28). It was assumed that two-domain enzymes like I-SceI (29) or I-DmoI (18) arose from the one-domain homing endonucleases like I-CreI (17) and I-CeuI (30) by a gene duplication event (3,4,21,23,31).

Some proteins with two LAGLIDADG (SEQ ID NO: 17) motifs are involved in splicing of their intron RNA. They are termed maturases (32,33). Maturases act as cofactors and stabilize the catalytic core of the intronic RNA structure for the splicing event (34,35). Some dodecapeptide endonucleases also bear a latent maturase activity, which can be revealed by mutation of a few amino acids (36-38). Only few of them reveal both activities simultaneously, as it was reported for I-AniI (39,40) and I-ScaI (41-43).

In the mitochondrial cox1 gene of *Schizosaccharomyces pombe* up to 4 group I-introns were found (44). Two of them contain open reading frames encoding proteins of the dodecapeptide family (45,46).

In summary, there exists a need in the art for reagents and methods for providing transgenic animal models of human diseases and genetic disorders. The reagents can be based on a restriction enzyme, especially with high specificity, its corresponding restriction site, and the gene encoding this enzyme. In particular, there exists a need for reagents and methods for replacing a natural gene or fragment thereof, with another gene or gene fragment that is capable of alleviating the disease, or is capable, by modifying the cell or animal, to offer molecular tools to study such diseases.

SUMMARY OF THE INVENTION

Accordingly, this invention aids in fulfilling these needs in the art Specifically, this invention relates to an isolated DNA encoding the enzyme I-SpomI.

In one embodiment of the invention, a DNA sequence comprising a promoter operatively linked to the DNA sequence of the invention encoding the enzyme I-SpomI is provided This invention further relates to an isolated RNA complementary to the DNA sequence of the invention encoding the enzyme I-SpomI and to the other DNA sequences described herein.

In another embodiment of the invention, a vector is provided The vector can be a plasmid, bacteriophage, cosmid, or viral, particularly retroviral, vector containing the DNA sequence of the invention encoding the enzyme I-SpomI.

In another embodiment of the invention, the vector can comprise a plasmid, bacteriophage, cosmid, or viral, particularly retroviral, vector containing the DNA sequence of the invention encoding an I-SpomI restriction site.

The invention also relates to a method for generating recombinant chromosomes and cells containing an I-SpomI restriction site. In one embodiment, the I-SpomI restriction site is introduced by recombination.

The invention further relates to a method for generating recombinant chromosomes and cells expressing I-SpomI enzyme. In one embodiment, a sequence coding for I-SpomI enzyme is introduced by recombination.

The invention also relates to a recombinant chromosome comprising an I-SpomI site or a DNA sequence encoding the enzyme I-SpomI. The recombinant chromosome can be from a prokaryotic or eukaryotic organism. In one embodiment, the invention relates to a recombinant mammalian, yeast, fungal, bacterial, plant, nematode, or insect chromosome. In a preferred embodiment, the invention relates to a recombinant *drosophila, C. elegans*, plant, or mouse chromosome.

In addition, this invention relates to prokaryotic, for example *E. coli*, or eukaryotic cells transformed with a vector of the invention. In one embodiment, the invention relates to a mammalian, yeast, fungal, bacterial, plant, nematode, or insect cell transformed with a vector of the invention. In a preferred embodiment, the invention relates to a recombinant *drosophila, C. elegans* plant, or mouse cell transformed with a vector of the invention. In another embodiment the cells are stem cells, preferably mammalian stem cells and most preferably mouse stem cells. The invention further relates to cell lines derived from these cells.

Also, this invention relates to transgenic organisms containing the DNA sequence encoding the enzyme I-SpomI and cell lines cultured from cells of the transgenic organisms.

In addition, this invention relates to a transgenic organism in which at least one restriction site for the enzyme I-SpomI has been inserted in a chromosome of the organism Further, this invention relates to a method of genetically mapping a eukaryotic genome using the enzyme I-SpomI.

This invention also relates to a method for in vivo site directed recombination in an organism using the enzyme I-SpomI.

BRIEF DESCRIPTION OF THE DRAWINGS

This invention will be more fully described with reference to the drawings in which:

FIG. 1 depicts plasmid inserts.

A PCR-fragment spanning the 1560 nt of the entire reading frame starting at the exon and ranging to the stop codon in the intron cox1I1b was cloned into pET16b, giving plasmid pSP001. Plasmid pSP005 lacks the entire 5'-exon part of the ORF, whereas pSP003 contained a fragment that is limited to the loop 8 part of the sequence. The restriction enzymes, which were used for the cloning, are indicated.

FIG. 2 depicts expression and purification of I-SpomI.

FIG. 2A. Purification chromatogram. His-tagged I-SpomI was expressed in *E. coli* as explained in the text. Subsequently to the *E. coli* cell-disruption, the supernatant was loaded onto a 1 ml HiTrap chelating affinity column (Amersham Pharmacia Biotech, Little Chalfont), charged with $Ni^{2+}$ and equilibrated with lysis buffer (30 mM HEPES pH8, 300 mM NaCl, 20 mM Imidazole) at a flow rate of 1 ml/min. The I-SpomI endonuclease is bound via its N-terminal His-tag while impurities are washed out with lysis buffer. Elution of the proteins was performed by increasing the imidazole concentration within the buffer, measured by conductivity. The endonuclease band was found in the fraction washed out of the column at an imidazole concentration of 200 mM. Absorbance at $\lambda=260$ nm and $\lambda=280$ nm was monitored.

FIG. 2B. 12% SDS-PAGE of the peak fractions 4 to 11. Fraction 6 was used for the assays.

FIG. 2C. Western blot of I-SpomI preparation after affinity chromatography. The band of the truncated protein appeared above the 36.5 kDa band of the unstained New England Biolabs Broad Range marker, which correlates well to the expected size of 38.7 kDa.

FIG. 3 depicts determination of the cleavage site of I-SpomI.

Figure 3A:
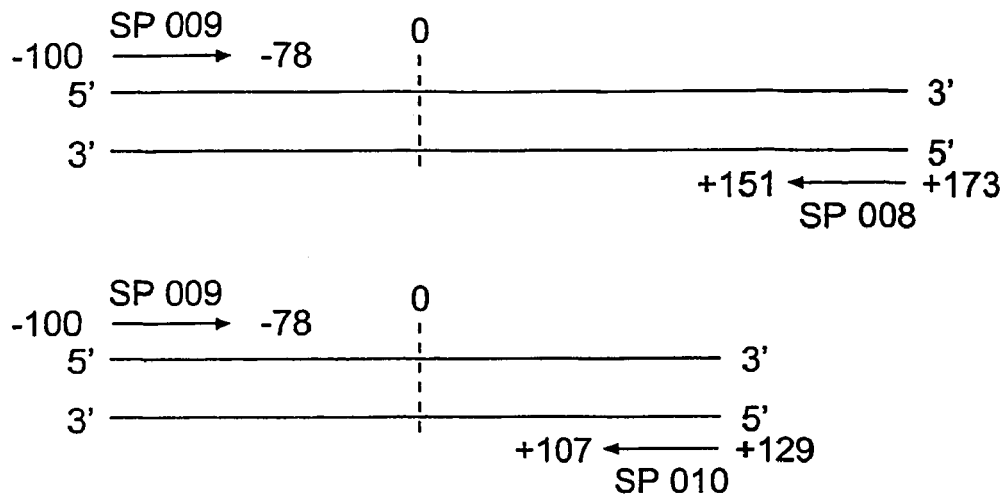

FIG. 3A. Primers used for generating 5' end-labeled I-SpomI-substrates. Both ends of each oligonucleotide are numbered according to the distance from the intron insertion site.

Figure 3B:
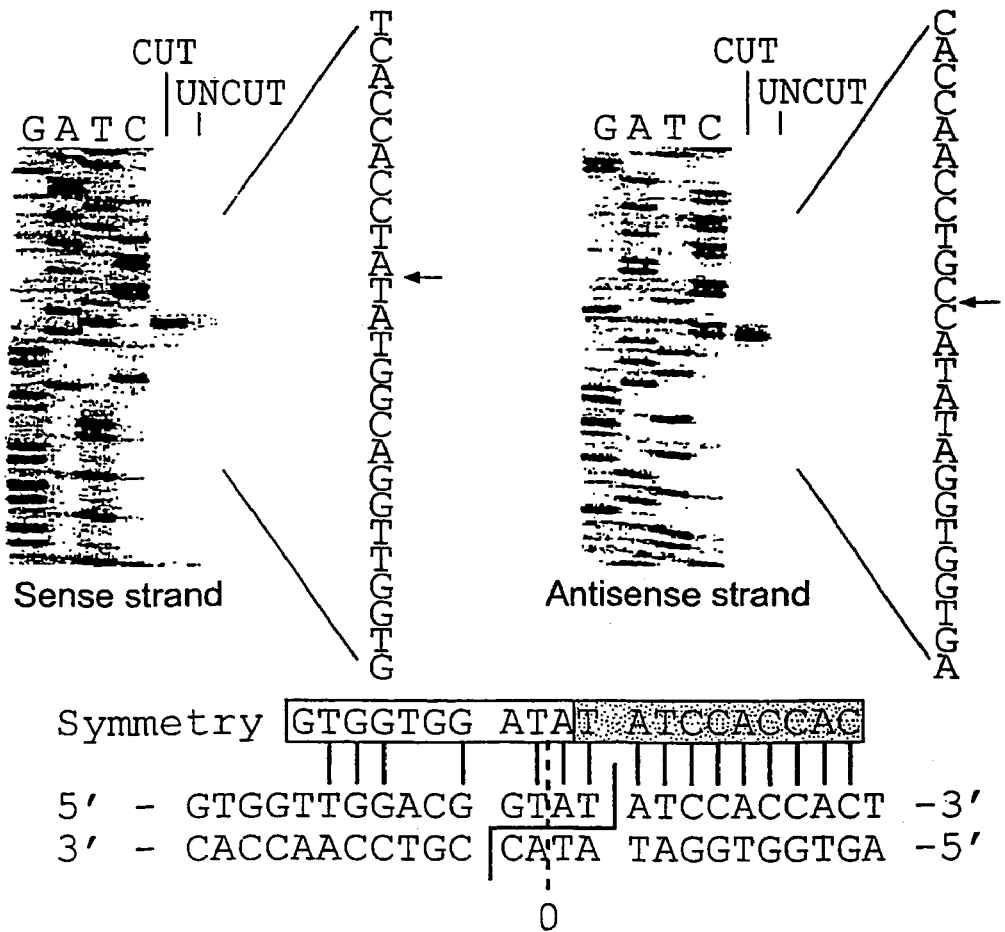

FIG. 3B. Cleavage site of I-SpomI. Two different end-labeled DNA templates were prepared by PCR reactions using $5'-\gamma^{32}P$ end-labeled primers SP009, SP008 or SP010. The DNA substrates were then incubated with I-SpomI. After cleavage, DNA-fragments were electrophorized on a sequencing gel next to a sequencing ladder of the same DNA sequence. Arrows indicate cleavage of the phosphodiester bond on the sense strand (left) (SEQ ID NO: 15) and the antisense strand (right) (SEQ ID NO: 16). The cleavage pattern is summarized in the figure underneath (SEQ ID NOS: 14-16, respectively in order of appearance), represented by the staggered line, the dotted line shows the position of the intron insertion site. The sequence of the site shows partial symmetry.

FIG. 4. depicts determination of optimal conditions for I-SpomI cleavage. % cleaved product is expressed by the ratio between the signal from the 173 bp long cleaved fragment to the sum signal (signal of this fragment plus the radioactivity of the 273 bp uncleaved substrate).

Figure 4A:
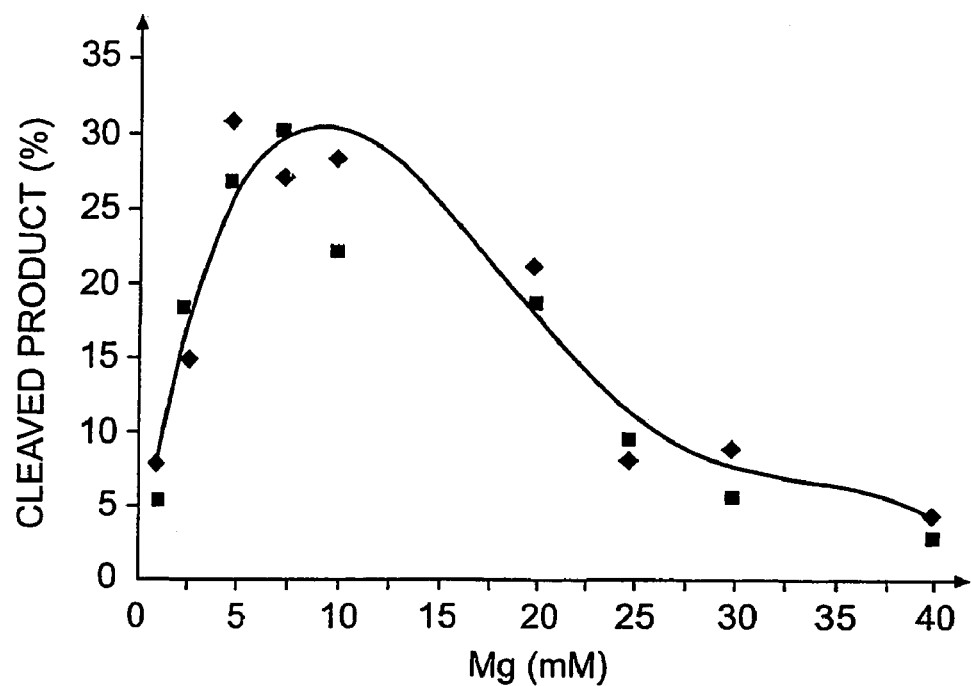

FIG. 4A. $Mg^{2+}$-concentration. 1 μl of the PCR-product SP009-SP008 was incubated in a total volume of 25 μl with 5 μl of I-SpomI-solution. The reaction buffer contained 0.1M Diethanolamine/HCl at pH9.0, 0.1M NaCl and $MgCl_2$ in various concentrations between 1 mM and 40 mM. The reactions were carried out for 20 min at 37° C.

Figure 4B:
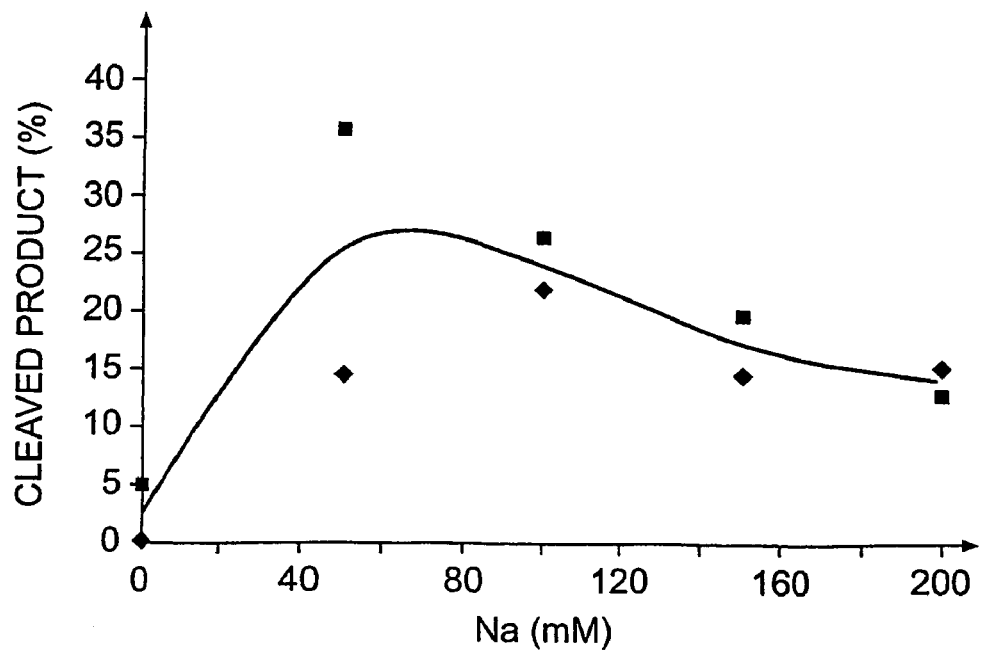

FIG. 4B. $Na^+$-concentration. The Reaction volume and the added volume of the PCR-product were as described under A. The reaction buffer contained 0.1M Diethanolamine/HCl at pH9.0, $MgCl_2$ 2.5 mM and NaCl in different concentrations between 0M and 0.2M. The reactions were incubated for 20 min at 37° C.

Figure 4C:
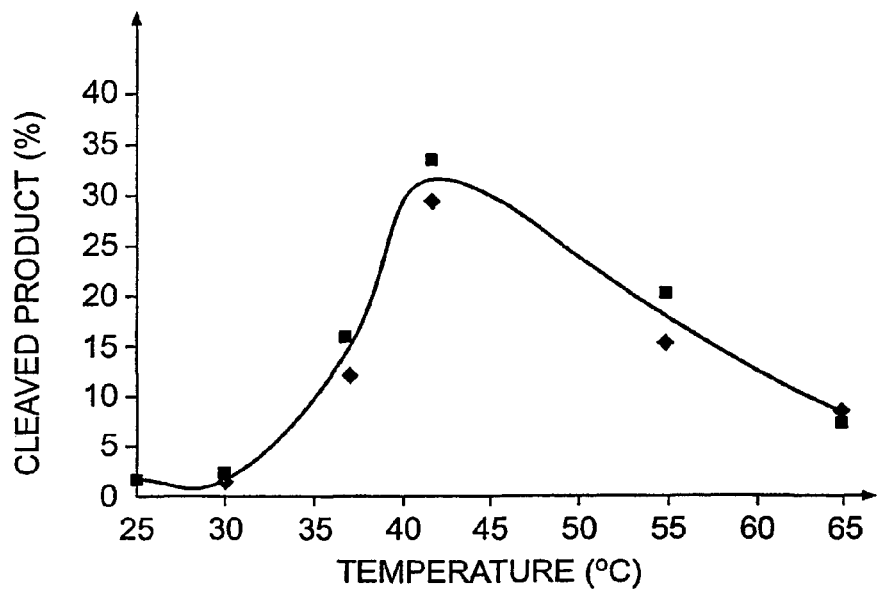

FIG. 4C. Temperature. The Reaction volume and the added volume of the PCR-product were as described under A. The reaction buffer contained 0.1M Diethanolamine/HCl at pH9.0, $MgCl_2$ 2.5 mM and NaCl 0.1M. The reactions were incubated for 20 min at temperatures between 25° C. and 65° C.

Figure 4D:
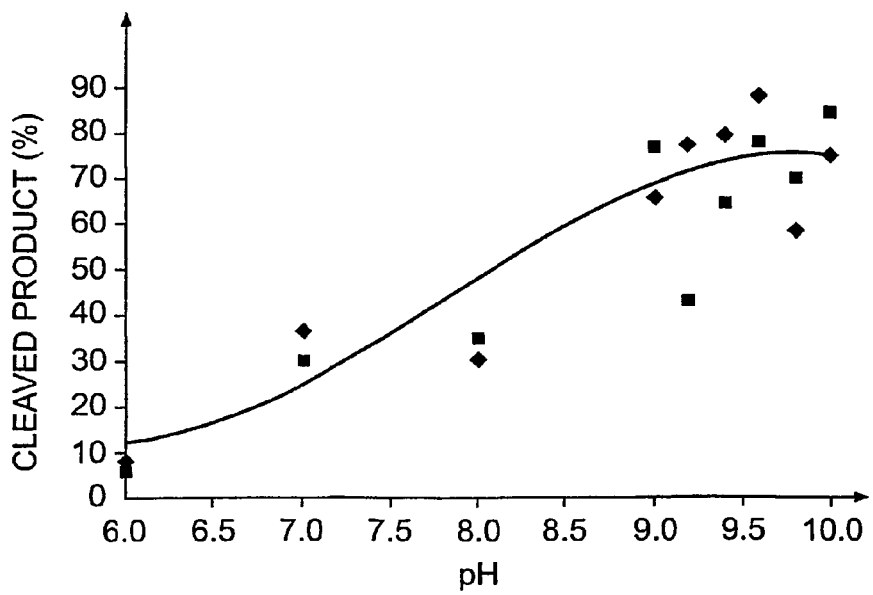

FIG. 4D. pH. The Reaction volume and the added volume of the PCR-product were as described under A. The reaction buffer contained 0.03M MES at pH 6.0, 0.1M HEPES at pH 7.0 or pH 8.0, 0.1M Diethanolamine/HCl at pH9.0, 9.2, 9.4, 9.6, 9.8 or pH 10, $MgCl_2$ 2.5 mM and NaCl 0.1M. The reactions were incubated for 20 min at 37° C.

Note that the assays for $Mg^{2+}$, $Na^+$ and temperature were performed with the same enzyme preparation. The maximum of cleaved product after 20 min of digestion at 37° C. was about 30% of the total DNA. Assays at different pH-value were performed with another enzyme preparation and the cleavage efficiency under optimal conditions was about 85%.

FIG. 5 depicts determination of the I-SpomI recognition sequence.

Figure 5A:
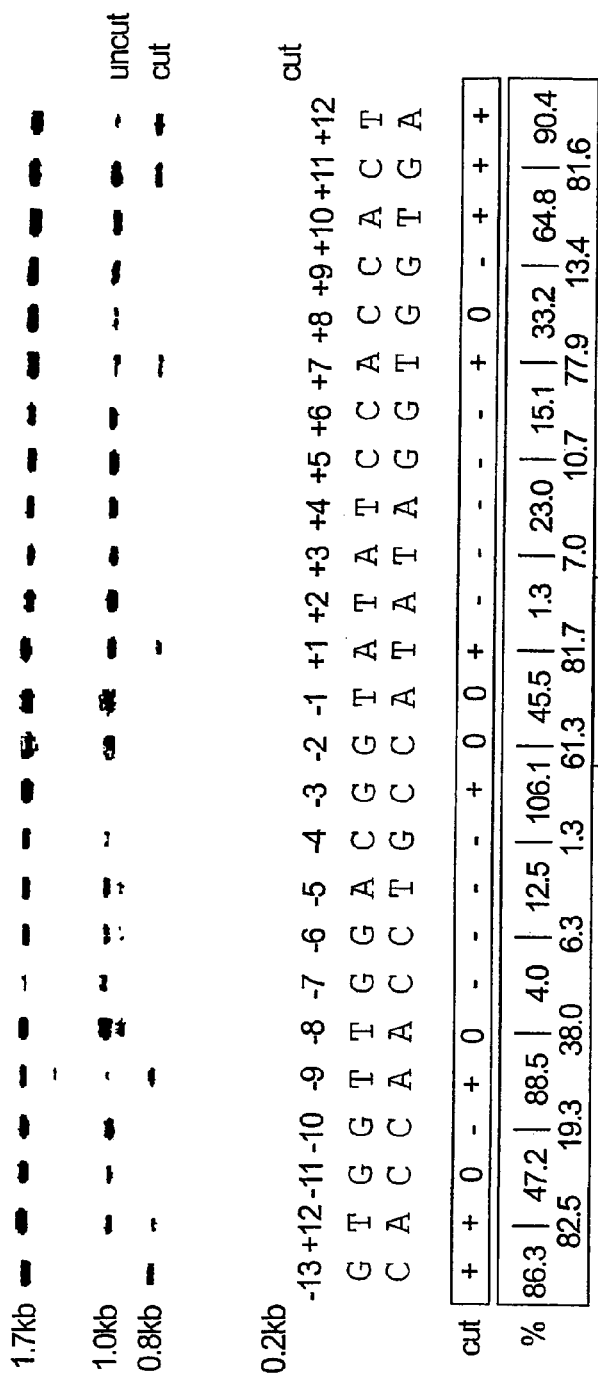

FIG. 5A. Electrophoretic analysis of NdeI-AlwNI fragments of plasmid pP3E5-2 after incubation with I-SpomI. DNA-fragments were revealed by Southern blotting and hybridization with random labeled pUC19. The 1 kb fragment contains the I-SpomI site, which generates two fragments of 0.8 kb and 0.2 kb respectively after cleavage by I-SpomI. For the assay, a set of plasmids was used, each plasmid containing a single nucleotide mutation of the wild type exon-exon sequence shown below. Each mutation corresponds to the transversion compared to the wild type sequence. Figure discloses SEQ ID NOS: 15-16, respectively, in order of appearance.

The staggered line indicates the cleavage site. In the box named "cut" the effect of each mutation is shown: +=the mutant is cleaved as well as the wild-type; 0=reduced cleavage; −=no cleavage. Percent values point out the relative cutting efficiency of I-SpomI on each mutated sequence relative to the wildtype sequence. Values represent the ratio in % between cleaved product and the mutated sequences for the wild type sequence. The 0.8 kb band is compared to the total DNA present in the 1.0 kb and the 0.8 kb bands.

Figure 5B:
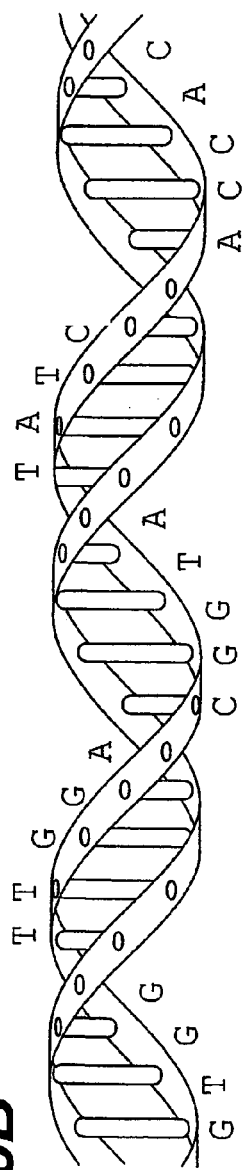

FIG. 5B. Helical representation of the DNA-region (Bases 1-24 of SEQ ID NO: 15). The arrows indicate the positions at which the strand breakage is introduced.

Figure 6:
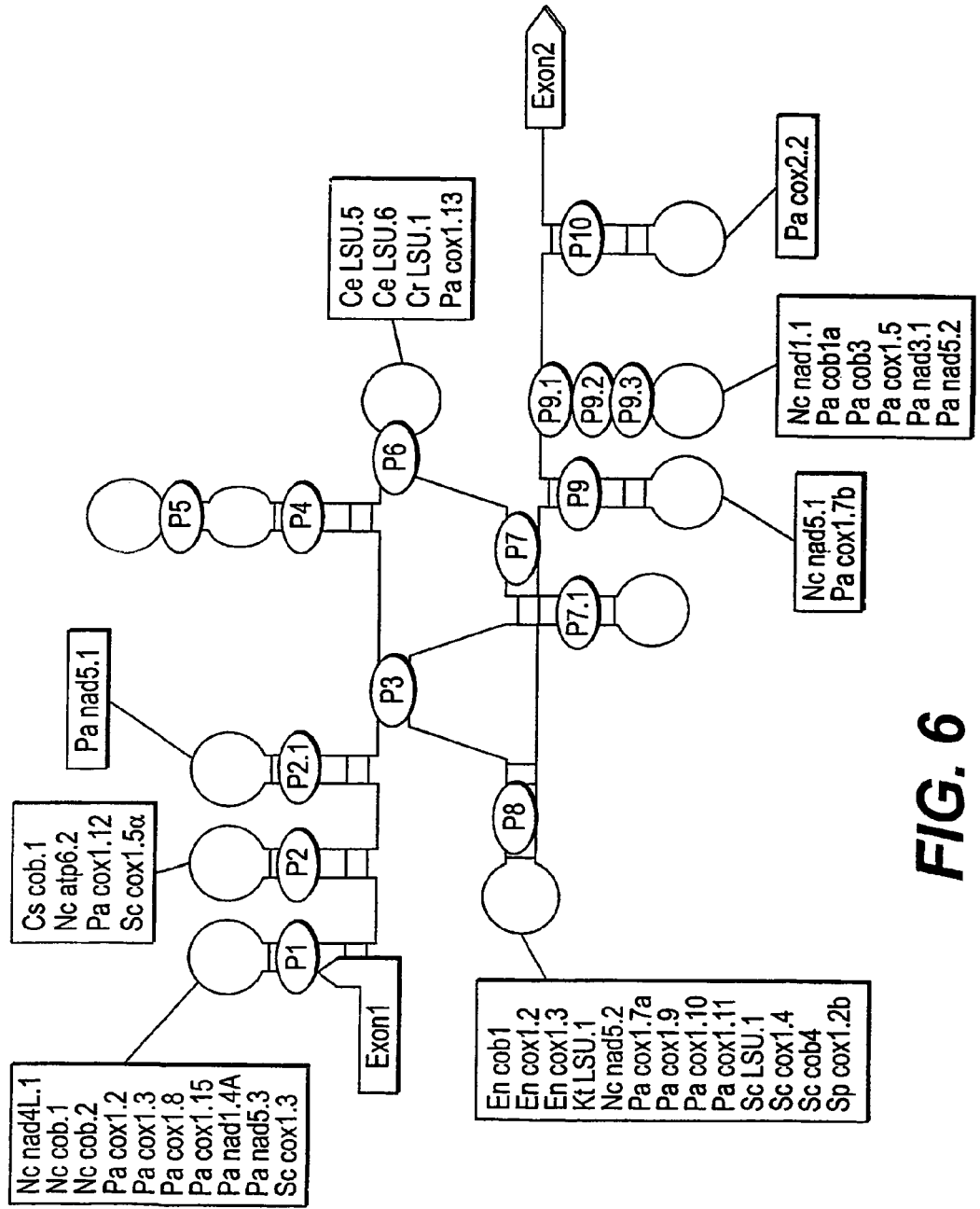

FIG. 6 depicts ORFs in peripheral loops of group I introns

The schematic diagram of the group I intron secondary structure shows the insertion sites of ORFs of LAGLIDADG (SEQ ID NO: 17) type proteins.

Ce: *Chlamydomonas eugametos*. Cr: *Chlamydomonas reinhardtii*. Cs: *Chlamydomonas smithii*. En: *Emericella nidulans*. Kt: *Kluyveromyces thermolerans*. Ne: *Neurospora crassa*. Pa: *Podospora anserina*. Sc: *Saccharomyces cerevisiae*. Sp: *Schizosaccharomyces pombe*.

FIG. 7 depicts the nucleotide sequence of the first exon of cox1 plus the intron coding for I-SpomI (SEQ ID NO:8).

FIG. 8 depicts a nucleotide sequence encoding the I-SpomI enzyme (SEQ ID NO:9).

FIG. 9 depicts the nucleotide sequence of an I-SpomI recognition site (SEQ ID NO:10).

FIG. 10 depicts the amino acid sequence of a natural I-SpomI protein (SEQ ID NO:11).

FIG. 11 depicts the amino acid sequence of an I-SpomI protein (SEQ ID NO:12).

DETAILED DESCRIPTION OF THE INVENTION

I-SpomI, the gene product of the first group I intron in the mitochondrial cox1 gene of *Schizosaccharomyces pombe*, is endowed with endonuclease activity. It recognizes the flanking sequence around the intron insertion within the intronless cox1 allele. Major modifications in the N-terminus of I-SpomI compared to the gene product of the native reading frame did not affect cutting capability nor sequence specificity of the endonuclease. The position of the start codon of homing endonucleases is variable and can be located in various parts of the host gene. There are representatives with an ORF in frame with the preceding exon sequence or others with a reading frame limited to the intron sequence or even those with an intronic ORF in an intron. Another basic question concerns whether the endonuclease needs to be modified or processed in order to become active. It has been reported for I-SceII (19) and I-SceIII (55) that they are synthesized as precursor proteins and then processed.

The inventors have determined that the sequence of loop 8 intronic secondary structure of cox1I1b in *S. pombe* encodes a protein that acts as a specific endonuclease in vitro. The sequence of I-SpomI can be found in Genebank, Accession numbers NC_001326 X00886 X02819 X15738 (gene="cox1"; intronic ORF) or X54421 X00886 X02819 X15738.

The optimum conditions for the in vitro activity of I-SpomI bear a striking resemblance to those preferred by I-SceI (29). The preference for high pH values between 9.0 and 10.0 is rather unusual. For example, I-ScaI (43) shows best activity at pH8.0 to 9.0 and I-CreI (51) between pH7.0 and 9.0. A characteristic feature shared with other LAGLIDADG (SEQ ID NO: 17) endonucleases is the dependence on the divalent cation $Mg^{2+}$, but the influence of other cofactors like $Mn^{2+}$ or $Zn^{2+}$ on cutting activity was not checked.

The cleavage pattern of I-SpomI shows the typical 3'-overhang of 4 nt length as it has been described for many other endonucleases of the LAGLIDADG (SEQ ID NO: 17) type of different kingdoms, for example I-AniI (39), I-ScaI (43), I-SceI (16), II (37) and III (56) I-CeuI (30), I-ChuI (57), I-CreI (17), I-CpaII (58), I-DmoI (20), I-PorI (59), PI-SceI (60), PI-ThyI (61), PI-TliI (62) and PI-TfuII (63) and also the HO endonuclease of *S. cerevisiae* (64). I-SpomI cleaves the sense strand and the antisense strand 2 nt away from the intron insertion site. The recognition site of I-SpomI is 20 nt in length. Four bases in the middle of the site, almost identical with the position of the endonucleolytic cut of the enzyme, are not needed for substrate recognition as it has been reported for I-CreI as well (65). They are flanked by five essential nucleotides on each side. On each margin of the required sequence another two bases are present, which can not be changed (FIG. 5A). Therefore, 14 single mutations between positions −11 and +9 affect cleavage. Like other intron encoded homing endonucleases, I-SpomI recognizes a long DNA sequence although the protein is rather small in comparison to bacterial restriction endonucleases. Bacterial type II restriction enzymes engulf the DNA and nearly saturate the hydrogen bond donors in the major groove and in addition they often contact the minor groove of the recognition site (26). Since the profile of intron encoded homing endonucleases, based on β-sheets, is flat, they interact with the specific bases of the recognition site over the DNA major groove without using additional chains so that they make subsaturating contacts (4). According to the recognition pattern, for I-SpomI, the inventors hypothesize a contact to the substrate DNA from one side in which the catalytic domain of the enzyme faces the minor DNA groove while the two recognition domains face the neighboring major grooves. This also explains the independence of recognition on the four central bases, flanked by essential bases. Although the order of essential and non-essential nucleotides within the I-SpomI recognition site is symmetric, there is no palindromic sequence present like for homodimeric LAGLIDADG (SEQ ID NO: 17) enzymes like I-CreI (66). In general, endonuclease domains of monomeric dodecapeptide endonucleases bear a pronounced asymmetry in comparison to the homodimeric enzymes. This causes relaxed symmetry requirement for the recognition site and allows the acquisition of an expanded range of substrates (3,67). Recognition and cutting sequences of the dodecapeptide homing endonucleases are highly divergent.

According to an alignment of 131 LAGLIDADG (SEQ ID NO: 17) proteins (10), I-AniI (39) is the closest relative to I-SpomI, but neither cutting nor recognition sites resemble those of I-SpomI.

Homing endonuclease ORFs occur in different peripheral loops of the RNA secondary structure of group I introns after invasion of these exposed loops (2,68-70). Thus, the intron and the intronic ORF are regarded as independent genetic elements (71). For the GIY-YIG enzyme I-TevII, an alignment of exon junction sequences of the phage T4 sunY gene and intron sequences flanking the ORF in loop L9.1 revealed a high degree of similarity spanning the I-TevII recognition sequence (72). This finding and the independence of intron mobility on DNA encoding the catalytic core sequences, when applying the endonuclease in trans (73), supports the hypothesis of intron invasion ORFs of dodecapeptide homing endonucleases are inserted in loops L1 (I-SceIII (56)), L2 (I-SceIV (28), I-SceVII (74), I-ScaI (41)), L6 (I-CeuI (30), I-CreI (75)) and L8 (I-AniI (39,74), I-DdiI (71) (76), I-SceI (16,74), I-SceII (19,74)) (FIG. 6).

The recently purified I-ScaI was the first reported protein to have both endonuclease and maturase activity, whereas the maturase homologue in intron bi2 of the cyt b gene in *S. cerevisiae* is dependent on a replacement of two non-adjacent amino acids to gain the endonuclease activity (38,41,42). Another protein containing both activities is I-AniI, encoded by a mitochondrial group I intron in *Emericella nidulans* (39). Proteins that contain both activities might represent intermediates in this evolution.

Based on multiple sequence alignment of LAGLIDADG-enzymes (SEQ ID NO: 17) from different kingdoms, it has been suggested before that exchange of endonucleases between different genes and between various hosts is very unlikely (10). Instead, the acquisition of these mobile elements has occurred many times independently and not only once in a common ancestor. Since the original introns are self-splicing, an endonuclease ORF must insert into a peripheral loop of the intron secondary structure to maintain the essential ribozyme functional (FIG. 6). The position of this invasion is therefore not dependent on the host organism or gene, but on the secondary structure of the respective intron. Nonetheless, insertion of an ORF into an intron may cause derogation of the self-splicing and gives rise to the necessity of a maturase protein to improve this process. It has been reported that none of the four group I introns in the cox1 of *S. pombe* splices autocatalytically in vitro, whereas autocatalytic splicing of the *S. cerevisiae* ml intron is observed (44), possibly because of the involvement of maturase proteins in the splicing procedure in vivo. In this work, the inventors have demonstrated that the enzyme core, including the two LAGLIDADG (SEQ ID NO: 17) motifs in the intron cox1I1b of *S. pombe*, is sufficient to gain endonuclease activity from I-SpomI, and concluded that the ancient ORF is still present in the insertion site in loop L8, but it is controlled by the start codon for the entire gene product.

I-SpomI Gene Sequence

This invention relates to an isolated DNA sequence encoding the enzyme I-SpomI. The enzyme I-SpomI is an endonuclease, especially a DNA endonuclease.

The first group I intron of the cox1 gene (cox1I1b) of the mitochondrial genome of the fission yeast *Schizosaccharomyces pombe* contains an open reading frame encoding a polypeptide, which is a typical member of the LAGLIDADG (SEQ ID NO: 17) protein family with two consensus motifs.

Biochemical characterization of the endonuclease activity of this protein artificially expressed in *E. coli* has been performed and a translation product of 304 codons of the cox1/1b ORF located in loop 8 of the intron RNA secondary structure exhibits a specific endonuclease activity in vitro. The optimal in vitro conditions for endonucleolytic cleavage were characterized, and using such conditions the cleavage and recognition site of the protein were determined. Consistent with the findings from other LAGLIDADG (SEQ ID NO: 17) proteins, I-SpomI generates a double-strand break with 4 nt 3'-overhangs near the intron insertion site and recognizes a novel sequence of 20 nucleotides.

It is preferred that the DNA sequence encoding the enzyme I-SpomI be in a purified form. In addition, it is preferred that the DNA sequence of the invention is free of extraneous proteins and lipids, and adventitious microorganisms, such as bacteria and viruses. The essentially purified and isolated DNA sequence encoding I-SpomI is especially useful for preparing expression vectors.

The gene of the invention can be prepared by the formation of 3'----->5' phosphate linkages between nucleoside units using conventional chemical synthesis techniques. For example, the well-known phosphodiester, phosphotriester, and phosphite triester techniques, as well as known modifications of these approaches, can be employed Deoxyribonucleotides can be prepared with automatic synthesis machines, such as those based on the phosphoramidite approach. Oligo- and polyribonucleotides can also be obtained with the aid of RNA polymerase and ligase using conventional techniques.

This invention of course includes variants of the DNA sequence of the invention exhibiting substantially the same properties as the sequence of the invention By this it is meant that DNA sequences need not be identical to the sequence disclosed herein For example, due to the known degeneracy of the genetic code, wherein more than one codon can encode the same amino acid, a DNA sequence can vary from that shown in FIG. 7 and still encode a protein having the same amino acid sequence as that encoded by FIG. 7. Variations can be attributable to single or multiple base substitutions, deletions, or insertions or local mutations involving one or more nucleotides not substantially detracting from the properties of the DNA sequence as encoding an enzyme having the cleavage properties of the enzyme I-SpomI.

It will also be understood that the present invention is intended to encompass fragments of the DNA sequence of the invention in purified form, where the fragments are capable of encoding enzymatically active I-SpomI. Activity can be determined as in the Examples. Accordingly, the tern "I-SpomI enzyme" is meant to include variants and fragments of the native protein retaining the ability to cleave the I-SpomI I restriction site.

The invention provides isolated and purified, or homogeneous, I-SpomI polypeptides, both recombinant and non-recombinant. Variants and derivatives of native I-SpomI proteins that retain the desired biological activity can be obtained by mutations of nucleotide sequences coding for native I-SpomI polypeptides. Alterations of the native amino acid sequence can be accomplished by any of a number of conventional methods. Mutations can be introduced at particular loci by synthesizing oligonucleotides containing a mutant sequence flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene, wherein predetermined codons can be altered by substitution, deletion, or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); Sambrook et al. (*Molecular Cloning: A Laboratory Manual*, 3 ed., Cold Spring Harbor Laboratory Press, 2001), and U.S. Pat. Nos. 4,518,584 and 4,737,462, all of which are incorporated by reference.

The DNA sequence of the invention coding for the enzyme I-SpomI can be amplified in the well known polymerase chain reaction (PCR), which is useful for amplifying all or specific regions of the gene. See e.g., S. Kwok et al., J. Virol., 61:1690-1694 (1987); U.S. Pat. No. 4,683,202; and U.S. Pat. No. 4,683,195. More particularly, DNA primer pairs of known sequence positioned 10-300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the DNA. The PCR reaction mixture can contain the DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the DNA at an elevated temperature, cooling of the reaction mixture, and polymerization with the DNA polymerase. Amplified sequences can be detected by the use of techniques known by those skilled in the art 2. Nucleotide Probes Containing the I-SpomI Gene of the Invention The DNA sequence of the invention coding for the enzyme I-SpomI can also be used as a probe for the detection of a nucleotide sequence in a biological material. The probe can be labeled with an atom or inorganic radical, most commonly using a radionuclide, or with any non-radioactive material commonly used in molecular biology experiments. Radioactive labels include $^{32}P$, $^{3}H$, $^{14}C$, or the like. Any radioactive label can be employed, which provides for an adequate signal and has sufficient half-life. Other labels include ligands that can serve as a specific binding member to a labeled antibody, fluoresces, chemiluminescers, enzymes, antibodies which can serve as a specific binding pair member for a labeled ligand, and the like. The choice of the label will be governed by the effect of the label on the rate of hybridization and binding of the probe to the DNA or RNA It will be necessary that the label provide sufficient sensitivity to detect the amount of DNA or RNA available for hybridization.

When the nucleotide sequence of the invention is used as a probe for hybridizing to a gene, the nucleotide sequence tested with the probe is preferably affixed to a water insoluble solid, porous support, such as nylon membrane. Hybridization can be carried out using labeled polynucleotides of the invention and conventional hybridization reagents. The particular hybridization technique is not essential to the invention The amount of labeled probe present in the hybridization solution will vary widely, depending upon the nature of the label, the amount of the labeled probe which can reasonably bind to the support, and the stringency of the hybridization. Generally, substantial excesses of the probe over stoichiometric will be employed to enhance the rate of binding of the probe to the fixed DNA or RNA.

Various degrees of stringency of hybridization can be employed. The more severe the conditions, the greater the complementarity that is required for hybridization between the probe and the polynucleotide for duplex formation. Severity can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

Preferred hybridization conditions include standard hybridization conditions, such as those described in Church and Gilbert, *Proc Natl Acad Sci USA,* 1984, April; 81(7): 1991-5, and Church and Gilbert, Prog Clin Biol Res, 1985, 177(2):17-21, both of which are specifically incorporated by reference.

3. Nucleotide Sequences Containing the Nucleotide Sequence Encoding I-SpomI

This invention also relates to the DNA sequence of the invention encoding the enzyme I-SpomI or an I-SpomI restriction site, wherein the nucleotide sequence is linked to other nucleic acids. The nucleic acid can be obtained from any source, for example, from plasmids, from cloned DNA or RNA or from natural DNA or RNA from any source, including prokaryotic and eukaryotic organisms. The nucleic acid can be a recombinant chromosome into which a nucleic acid encoding I-SpomI enzyme has been introduced. Similarly, the nucleic acid can be a recombinant chromosome into which an I-SpomI restriction site has been introduced. DNA or RNA can be extracted from a biological material, such as microbial cultures, biological fluids or tissue, by a variety of techniques including those described by Sambrook et al., *Molecular Cloning: A Laboratory Manual*, Cold Spring Harbor Laboratory, New York (2001). The nucleic acid will generally be obtained from a bacteria, yeast, virus, or a higher organism, such as a plant or animal. The nucleic acid can be a fraction of a more complex mixture, such as a portion of a gene contained in whole human DNA or a portion of a nucleic acid sequence of a particular microorganism. The nucleic acid can be a fraction of a larger molecule or the nucleic acid can constitute an entire gene or assembly of genes. The DNA can be in a single-stranded or double-stranded form. If the fragment is in single-stranded form, it can be converted to double-stranded form using DNA polymerase according to conventional techniques.

The DNA sequence of the invention can be linked to a structural gene. As used herein, the term "structural gene" refers to a DNA sequence that encodes through its template or messenger mRNA a sequence of amino acids characteristic of a specific protein or polypeptide. The nucleotide sequence of the invention can function with an expression control sequence, that is, a DNA sequence that controls and regulates expression of the gene when operatively linked to the gene.

4. Vectors Containing the Nucleotide Sequence of the Invention

This invention also relates to cloning and expression vectors containing the DNA sequence of the invention coding for the enzyme I-SpomI or an I-SpomI restriction site.

More particularly, the DNA sequence encoding the enzyme can be ligated to a vehicle for cloning the sequence. The major steps involved in gene cloning comprise procedures for separating DNA containing the gene of interest from prokaryotes or eukaryotes, cutting the resulting DNA fragment and the DNA from a cloning vehicle at specific sites, mixing the two DNA fragments together, and ligating the fragments to yield a recombinant DNA molecule. The recombinant molecule can then be transferred into a host cell, and the cells allowed to replicate to produce identical cells containing clones of the original DNA sequence.

The vehicle employed in this invention can be any single- or double-stranded DNA molecule capable of transporting the nucleotide sequence of the invention into a host cell. When the vehicle is also capable of replicating within the cell, it must contain at least one DNA sequence that can act as the origin of replication in the host cell. In addition, the vehicle must contain one or more sites for insertion of the DNA sequence encoding the gene of the invention. These sites will ordinarily correspond to restriction enzyme sites at which cohesive ends can be formed, and which are complementary to the cohesive ends on the promoter sequence to be ligated to the vehicle. In general, this invention can be carried out with plasmid, bacteriophage, cosmid vehicles, bacterial artificial chromosomes (BAC), or yeast artificial chromosomes (YAC) having these characteristics.

The nucleotide sequence of the invention can have cohesive ends compatible with any combination of sites in the vehicle. Alternatively, the sequence can have one or more blunt ends that can be ligated to corresponding blunt ends in the cloning sites of the vehicle. The nucleotide sequence to be ligated can be farther processed, if desired, by successive exonuclease deletion, such as with the enzyme Bal 31 or λ exo III. In the event that the nucleotide sequence of the invention does not contain a desired combination of cohesive ends, the sequence can be modified by adding a linker, an adaptor, or homopolymer tailing.

It is preferred that vehicles, for example plasmids, used for cloning nucleotide sequences of the invention carry one or more genes responsible for a useful characteristic, such as a selectable marker, displayed by the host cell. In a preferred strategy, vehicles having genes for resistance to two different drugs are chosen. For example, insertion of the DNA sequence into a gene for an antibiotic inactivates the gene and destroys drug resistance. The second drug resistance gene is not affected when cells are transformed with the recombinants, and colonies containing the gene of interest can be selected by resistance to the second drug and susceptibility to the first drug. Preferred antibiotic markers are genes imparting chloramphenicol, ampicillin, or tetracycline resistance to the host cell.

A variety of restriction enzymes can be used to cut the vehicle. The identity of the restriction enzyme will generally depend upon the identity of the ends on the DNA sequence to be ligated and the restriction sites in the vehicle. The restriction enzyme is matched to the restriction sites in the vehicle, which in turn is matched to the ends on the nucleic acid fragment being ligated.

The ligation reaction can be set up using well known techniques and conventional reagents. Ligation is carried out with a DNA ligase that catalyzes the formation of phosphodiester bonds between adjacent 5'-phosphate and the free 3'-hydroxy groups in DNA duplexes. The DNA ligase can be derived from a variety of microorganisms. The preferred DNA ligases are enzymes from *E. coli* and bacteriophage T4. T4 DNA ligase can ligate DNA fragments with blunt or sticky ends, such as those generated by restriction enzyme digestion. *E. coli* DNA ligase can be used to catalyze the formation of phosphodiester bonds between the termini of duplex DNA molecules containing cohesive ends.

Cloning can be carried out in prokaryotic or eukaryotic cells. The host for replicating the cloning vehicle will of course be one that is compatible with the vehicle and in which the vehicle can replicate. When a plasmid is employed, the plasmid can be derived from bacteria or some other organism or the plasmid can be synthetically prepared. The plasmid can replicate independently of the host cell chromosome or an integrative plasmid can be employed. The plasmid can make use of the DNA replicative enzymes of the host cell in order to replicate or the plasmid can carry genes that code for the enzymes required for plasmid replication. A number of different plasmids can be employed in practicing this invention.

The DNA sequence of the invention encoding the enzyme I-SpomI can also be ligated to a vehicle to form an expression vector. The vehicle employed in this case is one in which it is possible to express the gene operatively linked to a promoter in an appropriate host cell. It is preferable to employ a vehicle known for use in expressing genes in bacteria, for example *E. coli*, yeast, insect, fungi, nematode, plant, or mammalian cells.

Any alternative technique known to those skilled in the art Ban be used for modifying the vehicle.

Expression Systems

The present invention also provides recombinant cloning and expression vectors containing DNA, as well as host cell containing the recombinant vectors. Guidance can be found in laboratory guides such as Current Protocols in Molecular Biology (Ausubel et al., Wiley, 1998).

Expression vectors comprising DNA may be used to prepare the I-SpomI enzyme. A method for producing I-SpomI enzyme comprises culturing host cells transformed with a recombinant expression vector encoding the I-SpomI enzyme, under conditions that promote expression of the enzyme, then recovering the expressed enzyme, from the culture. The skilled artisan will recognize that the procedure for purifying the expressed enzyme will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding a peptide, for example an appropriate signal peptide (native or heterologous), can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian, nematode, plant, bacterial, fungal, yeast, or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides using RNAs derived from DNA constructs disclosed herein.

Prokaryotic Systems

Prokaryotes include grain-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement Examples of useful expression vectors for prolcaryotic host cells include those derived from commercially available plasmids such as the cloning vector pBR322 (ATCC 37017) or vectors derived from pBR322, such as vectors from the puC group. pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the *Saccharomyces* genus (e.g., *S. cerevisiae*). Other genera of yeast such as *Pichia* or *Kluyveromyces*, may also be employed. Yeast vectors will often contain an origin of replication sequence from a 2µ yeast plasmid, an autonomously replicating sequence (ARS), a promoter region, sequences for polyadenylation, sequences for transcription termination, and a selectable marker gene. Suitable promoter sequences for yeast vectors include, among others, galactose-regulated promoters such as GRAP1 sequence (*Molecular Genetics of Yeast*, John R. Johnston, Oxford University Press, 1994), promoters for metallothionein, 3-phosphoglycerate kinase (Hitzeman et al., *J. Biol. Chem.* 255: 2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). In yeast host cells, the vectors are preferably shuttle vectors. Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kinjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Leu$^+$ transformants in a selective medium, wherein the selective medium consists of 0.67% yeast nitrogen base, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 1% peptone, and 2% glucose. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T 3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15-69). Additional protocols using commercially available reagents, such as Lipofectamine lipid reagent (Gibco/BRL) or Lipofectamine-Plus lipid reagent, can be used to transfect cells (Felgner et al. *Proc. Natl. Acad. Sci. USA* 84:7413-7417, 1987). In addition, electroporation can be used to transfect mammalian cells using conventional precede such as those in Sambrook et al. (*Molecular Cloning: A Laboratory Manual,* 3 ed. Vol. 1-3, Cold Spring Harbor Laboratory Press, 2001). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind m site toward the Bgl I site located in the SV40 viral origin of replication site is included.

Additional control sequences shown to improve expression of heterologous genes from mammalian expression vectors include such elements as the expression augmenting sequence element EASE) derived from CHO cells (Morris et al., *Animal Cell Technology*, 1997, pp. 529-534 and PCT Application WO 97/25420) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enymology*, 1990). Exemplary expression vectors that employ dicistronic mRNAs are pTR-DC/GFP described by Mosser et al., *Biotechniques* 22:150-161, 1997, and p2A5I described by Morris et al. *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983) and Sambrook et al. (*Molecular Cloning: A Laboratory Manual*, Cold Spring Harbor Laboratory, New York, 2001), for example. A useful system for stable high level expression of mammalian cDNAs in C127 murine mammary epithelial cells can be constructed substantially as described by Cosman et al. (*Mol. Immunol.* 23:935, 1986). Additional useful mammalian expression vectors are described in EP-A-0367566, and in WO 91/18982, incorporated by reference herein.

Additional useful expression vectors, pFLAG® and pDC311, can also be used& FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Expression of I-SpomI may be either constitutive or inducible. If inducibility is desired, an inducible promoter may be used. Examples of inducible systems are given in Brown, U.S. Pat. No. 6,180,391; Yee et al., U.S. Pat. No. 6,133,027; Reeves, U.S. Pat. No. 5,965,440; and Filmus et al., U.S. Pat. No. 5,877,018.

Purification

The invention also includes methods of isolating and purifying the polypeptides and fragments thereof.

Isolation and Purification

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His, HA-GST, or other antigenic identification peptides, as well as Fc moieties.

In another preferred embodiment, the purification is accomplished by the Tap-Tag technique (Rigaut et al., *Nat. Biotechnol.* 1999 October; 17(10):1030-2).

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as anti-polypeptide antibodies or other proteins that interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptidebinding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacryamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

5. Cells and Chromosomes Containing Nucleic Acids of the Invention

The nucleic acids of the invention can be introduced into host cells using conventional techniques. For example, the nucleic acids can be introduced by calcium phosphate precipitation (Graham & Van Der Eb, Virology, 52:456-467, 1973; Chen & Okayama, Mol. Cell Biol., 7:2745-2752, 1987; Rippe et al., Mol. Cell Biol., 10:689-695, 1990) DEAE-dextran (Gopal., Mol. Cell Biol., 5:1188-1190, 1985), electroporation (Tur-Kaspa et al., Mol. Cell Biol., 6:716-718, 1986), direct microinjection (Harland & Weintraub, J. Cell Biol., 101:1094-1099, 1985), DNA-loaded liposomes (Nicolau & Sene, Biochim. Biophys. Acta, 721:185-190, 1982; Fraley et al., Proc. Natl. Acad. Sci. USA, 76:3348-3352, 1979) and lipofectamine-DNA complexes, cell sonication (Fechheimer et al., "Transfection of mammalian cells with plasmid DNA by scrape loading and sonication loading," Proc. Natl. Acad. Sci. USA, 84:8463-8467, 1987), gene bombardment using high velocity microprojectiles (Yang et al., Proc. Natl. Acad. Sci. USA, 87:9568-9572, 1990), and receptor-mediated transfection (Wu & Wu, Biochemistry, 27:887-892, 1988; Wu & Wu, J. Biol. Chem., 262:4429-4432, 1987). Viral vectors, as discussed below, can also be used.

Preferred cells are bacterial, plant, nematode, yeast, insect, and mammalian. Pure microbial cultures can be used. Particularly preferred are *drosophila* and mouse cells. Cells can be primary cells or a cell line. Cells can contain the nucleic acid integrated into the genome. Alternatively, the nucleic acid may remain unintegrated In a preferred embodiment, a recombinant mammalian or insect chromosome contains an integrated I-SpomI site. Particularly preferred is a *drosophila, C. elegans*, or murine chromosome.

In another preferred embodiment a recombinant bacterial, plant, nematode, yeast, mammalian, or insect chromosome contains an nucleic acid that expresses I-SpomI enzyme. Particularly preferred is a *drosophila, C. elegans*, or murine chromosome.

Cloning can be carried out in prokaryotic or eukaryotic cells. The host for replicating the cloning vehicle will of course be one that is compatible with the vehicle and in which the vehicle can replicate. Cloning is preferably carried out in bacterial or yeast cells, although cells of fungal; animal, and plant origin can also be employed. The preferred host cells for conducting cloning work are bacterial cells, such as *E. coli*. The use of *E. coli* cells is particularly preferred because most cloning vehicles, such as bacterial plasmids and bacteriophages, replicate in these cells.

In a preferred embodiment of this invention, an expression vector containing the DNA sequence encoding the nucleotide sequence of the invention operatively linked to a promoter is inserted into a mammalian cell using conventional techniques.

6. Viral Vectors (a) Adenovirus Vectors

One method for in vivo delivery involves the use of an adenovirus expression vector. Adenovirus has been used to efficiently deliver I-SceI to human cells (Anglana and Bacchetti, *Nucleic Acids Research* 27: 4276-4281, 1999). Adenovirus has also been used as a vector to deliver HO endonuclease (Nicolas et al., *Virology* 266: 211-244, 2000). Adenovirus vectors can be use to deliver nucleic acid encoding I-SpomI enzyme.

Knowledge of the genetic organization or adenovirus, a 36 kB, linear, double-stranded DNA virus, allows substitution of large pieces of adenoviral DNA with foreign sequences up to 7 kB (Grunhaus & Horwitz, Adenovirus as cloning vector, Seminar in *Virology* 3: 237-252, 1992). The adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. Adenovirus is particularly suitable for use as a gene transfer vector because of its mid-sized genome, ease of manipulation, high titer, wide target-cell range and high infectivity. Generation and propagation of adenovirus vectors, which are replication deficient, depend on a helper cell line, which constitutively expresses adenovirus proteins (e.g. Graham et al., "Characteristics of a human cell line transformed by DNA from human adenovirus type 5," *J. Gen. Virol.* 36: 59-79, 1977).

Adenovirus vectors have been used in eukaryotic gene expression (Levrero et al., "Defective and nondefective adenovirus vectors for expressing foreign genes in vitro and in vivo," *Gene* 101: 195-202, 1991; Gomez-Foix et al., "Adenovirus-mediated transfer of the muscle glycogen phosphorylase gene into hepatocytes confers altered regulation of glycogen," *J. Biol. Chem.* 267: 25129-25134, 1992) and vaccine development (Grinhaus & Horwitz, Seminar in Virology, 3:237-252, 1992; Graham & Prevec, "Adenovirus-based expression vectors and recombinant vaccines," *Biotechnology* 20: 363-390, 1992). Animal studies have suggested that recombinant adenovirus can be used for gene therapy (Stratford-Perricaudet & Perricaudet p. 51-61, In: Human Gene Transfer, Cohen-Haguenauer & Boiron (eds.), Editions John Libbey Eurotext, France, 1991.; Stratford-Perricaudet et al., *Hum. Gene Ther.* 1: 241-256, 1990). Studies in administering recombinant adenovirus to different tissues include trachea instillation (Rosenfeld et al., "Adenovirus-mediated transfer of a recombinant .alpha.1-antitrypsin gene to the lung epithelium in vivo," *Science* 252: 431-434, 1991; Rosenfeld et al., "In vivo transfer of the human cystic fibrosis transmembrane conductance regulator gene to the airway epithelium," *Cell* 68: 143-155, 1992.), muscle injection (Ragot et al., "Efficient adenovirus-mediated transfer of a human minidystrophin gene to skeletal muscle of mdx mice," *Nature* 361: 647-650, 1993), peripheral intravenous injections (Herz & Gera "Adenovirus-mediated transfer of low density lipoprotein receptor gene acutely accelerates cholesterol clearance in normal mice," *Proc. Natl. Acad. Sci. USA* 90: 2812-2816, 1993) and stereotactic inoculation into the brain (Le Gal La Salle et al., "An adenovirus vector for gene transfer into neurons and glia in the brain," *Science* 259:988-990, 1993).

(b) Retrovirus Vectors

Retroviral vectors can be used to deliver nucleic acid encoding I-SpomI enzyme or an I-SpomI site to cells. The use of a retroviral vector facilitates integration of the nucleic acid into a host chromosome.

The retroviruses are a group of single-stranded RNA viruses characterized by an ability to convert their RNA to double-stranded DNA in infected cells by a process of reverse-transcription (Coffin, "Retroviridae and their replication," In: Virology, Fields et al. (eds.), New York: Raven Press, pp. 1437-1500, 1990). The resulting DNA then stably integrates into cellular chromosomes as a provirus and directs synthesis of viral proteins. The integration results in the retention of the viral gene sequences in the recipient cell and its descendants. In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., "Construction of a retrovirus packaging mutant and its use to produce helper-free defective retrovirus," Cell 33:153-159, 1983). When a recombinant plasmid containing a human cDNA, together with the retroviral LTR and packaging sequences is introduced into this cell line, the packaging sequence allows the RNA transcript of the recombinant plasmid to be packaged into viral particles, which are then secreted into the culture media (Nicolas & Rubenstein, "Retroviral vectors," In: Vectors: A survey of molecular cloning vectors and their uses, Rodriguez & Denhardt (eds.), Stoneham: Butterworth, pp. 493-513, 1988; Temin, In: Gene Transfer, Kucherlapati (ed.), New York: Plenum Press, pp. 149-188, 1986; Mann et al., Cell, 33:153-159, 1983). The media containing the recombinant retroviruses is then collected, optionally concentrated, and used for gene transfer. Retroviral vectors are able to infect a broad variety of cell types.

(c) Other Viral Vectors as Expression Constructs

Other viral vectors may be employed as expression or delivery constructs in the present invention. Vectors derived from viruses such as vaccinia virus (Ridgeway, "Mammalian expression vectors," In: Vectors: A survey of molecular cloning vectors and their uses, Rodriguez & Denhardt (eds.), Stoneham: Butterworth, pp. 467-92, 1988; Baichwal & Sugden, "Vectors for gene transfer derived from animal DNA viruses: Transient and stable expression of transferred genes," In: Gene transfer, Kucherlapati (ed), New York: Plenum Press, pp. 117-148, 1986; Coupar et al., "A general method for the construction of recombinant vaccinia virus expressing multiple foreign genes," Gene, 68:1-10, 1988) adeno-associated virus (AAV) (Ridgeway, Rodriguez & Denhardt (eds.), Stoneham: Butterworth, pp. 467-92, 1988; Baichwal & Sugden, La: Gene transfer, Kucherlapati (ed.), New York: Plenum Press, pp. 117-148, 1986) and herpes viruses may be employed.

Other vectors are disclosed in Segal et al. (*Proc. Natl. Acad. Sci. USA* 92: 806-810, 1995) for *Xenopus oocytes*, Machida et al. (*Proc. Natl. Acad. Sci. USA* 94:8675-8680, 1997) and Kirik et al (EMBO 19(20):5562-5566 (2000) for plants, and Bellaiche et al. (*Genetics* 152:1037-1044, 1999) for *drosophila*, for example.

7. Stem Cells

In one embodiment, stem cells containing nucleic acid encoding I-SpomI enzyme or an I-SpomI site can be prepared The routine insertion of specific genes into the mouse genome can be accomplished through the use of mouse ES cells (see e.g. Kusakabe et al., U.S. Pat. No. 6,190,910). Mouse ES cells are undifferentiated, pluripotent cells derived in vitro from preimplantation embryos (Evans, et al. Nature 292: 154-159, 1981; Martin, Proc. Natl. Acad. Sci. USA 78: 7634-7638, 1981) or from fetal germ cells (Matsui, et al., Cell 70: 841-847, 1992). Mouse ES cells maintain an undifferentiated state through serial passages (Williams, et al., Nature 336: 684-687, 1988).

Mouse ES cells combined into chimeras with normal pre-implantation embryos and returned to the uterus participate in normal development (Richard, et al., Cytogenet. Cell Genet. 65: 169-171, 1994). The ability of mouse ES cells to contribute to functional germ cells in chimeras provides a method for introducing site-specific mutations into mouse lines. With appropriate transfection and selection strategies, homologous recombination can be used to derive ES cell lines with planned alterations of specific genes (see, e.g., Jaisser et al., U.S. Pat. No. 5,830,729). These genetically altered cells can be used to form chimeras with normal embryos and chimeric animals are recovered. If the ES cells contribute to the germ line in the chimeric animal, then in the next generation a mouse line for the planned mutation is established. In a preferred embodiment, the mouse D3 embryonic stem cell line is used. Other ES cells, such as bovine stem cells (Sims et al. U.S. Pat. No. 6,107,543), can similarly be used.

8. Transgenic Animals

To create transgenic animals, conventional techniques can be used. In one embodiment, ES cells can be used to generate transgenic animals. In another embodiment, plasmids encoding I-SpomI enzyme or an I-SpomI restriction site can be injected into the male pronuclei of fertilized one-cell mouse eggs. The injected eggs can then transferred to pseudo-pregnant foster females. The eggs in the foster females are allowed to develop to term.

Transgenic animals carry a gene which has been introduced into the germline of the animal, or an ancestor of the animal, at an early (usually one-cell) developmental stage. Wagner et al. (1981) P.N.A.S. USA 78: 5016; and Stewart et al. (1982) Science 217, 1046 describe transgenic mice containing human globin genes. Constantini et al. (1981) Nature 294, 92; and Lacy et al. (1983) Cell 34, 343 describe transgenic mice containing rabbit globin genes. McKnight et al. (1983) Cell 34, 335 describes transgenic mice containing the chicken transferrin gene. Brinster et al. (1983) Nature 306, 332 describes transgenic mice containing a functionally rearranged immunoglobulin gene. Palmiter et al. (1982) Nature 300, 611 describes transgenic mice containing the rat growth hormone gene fused to a heavy metal-inducible metallothionein promoter sequence. Palmiter et al. (1982) Cell 29, 701 describes transgenic mice containing a thymidine kinase gene fused to a metalothionein promoter sequence. Palmiter et al. (1983) Science 222, 809 describes transgenic mice containing the human growth hormone gene fused to a metalothionein promoter sequence.

9. The Nested Chromosomal Fragmentation Strategy

The nested chromosomal fragmentation strategy for genetically mapping a eukaryotic genome exploits the unique properties of the restriction endonuclease I-SpomI, such as a 20 bp long recognition site. The absence of natural I-SpomI recognition sites in most eukaryotic genomes is also exploited in this mapping strategy.

First, one or more I-SpomI recognition sites are artificially inserted at various positions in a genome, by homologous recombination using specific cassettes containing selectable markers or by random insertion, as discussed supra. The genome of the resulting transgenic strain is then cleaved completely at the artificially inserted I-SpomI site(s) upon incubation with the I-SpomI restriction enzyme. The cleavage produces nested chromosomal fragments.

The chromosomal fragments are then purified and separated by pulsed field gel (PFG) electrophoresis, allowing one to "map" the position of the inserted site in the chromosome. If total DNA is cleaved with the restriction enzyme, each artificially introduced I-SpomI site provides a unique "molecular milestone" in the genome. Thus, a set of transgenic strains, each carrying a single I-SpomI site, can be created which defines physical genomic intervals between the milestones. Consequently, an entire genome, a chromosome or any segment of interest can be mapped using artificially introduced I-SpomI restriction sites.

The nested chromosomal fragments may be transferred to a solid membrane and hybridized to a labeled probe containing DNA complementary to the DNA of the fragments. Based on the hybridization banding patterns that are observed, the eukaryotic genome may be mapped. The set of transgenic stains with appropriate "milestones" is used as a reference to map any new gene or clone by direct hybridization 10. In Vivo Site Directed Recombination In a haploid cell, a single break within a chromosome at an artificial I-SpomI site results in cell division arrest followed by death (only a few % of survival). Presence of an intact sequence homologous to the cut site results in repair and 100% cell survival. In a diploid cell, a single break within a chromosome at an artificial I-SpomI site results in repair using the chromosome homolog and 100% cell survival. In both cases, repair of the induced double strand break results in loss of heterozygosity with deletion of the non homologous sequences flanking the cut and insertion of the non homologous sequences from the donor DNA molecule. Fairhead and Dujon, *Mol. Gen. Genet.* 240: 170-180 (1993).

Several strategies can be attempted for the site specific insertion of a DNA fragment from a plasmid into a chromosome. This will make it possible to insert transgenes at predetermined sites without laborious screening steps. Strategies are:

1-Construction of a transgenic cell in which the I-SpomI recognition site is inserted at a unique location in a chromosome. Expression of I-SpomI enzyme in the transgenic cell, and introduction of a nucleic acid molecule containing the gene of interest and a segment homologous to the sequence in which the I-SpomI site is inserted.

Expression of I-SpomI enzyme can be accomplished by many techniques, including direct introduction of active enzyme (e.g., microinjection, electroporation, scrape-loading of protein) and expression of protein from an inducible or constitutive viral or plasmid vector (e.g., adenoviral or retroviral vector).

2-Insertion of the I-SpomI recognition site next to or within the gene of interest carried on a plasmid. Cotransformation of a normal cell with the expression vector carrying the synthetic I-SpomI gene and the plasmid containing the I-SpomI recognition site.

3-Construction of a stable transgenic cell line in which the I-SpomI gene has been integrated in the genome under the control of an inducible or constitutive cellular promoter. Transformation of the cell line by a plasmid containing the I-SpomI site next to or within the gene of interest.

Site Directed Homologous Recombination:

1. Site Specific Gene Insertion

The methods allow the production of an unlimited number of cells and cell lines in which various genes or mutants of a given gene can be inserted at the predetermined location defined by the previous integration of the I-SpomI site. Such cells and cell lines are thus useful for screening procedures, for phenotypes, ligands, drugs and for reproducible expression at a very high level of recombinant retroviral vectors if the cell line is a transcomplementing cell line for retrovirus production.

Above cell lines are initially created with the I-SpomI site being heterozygous (present on only one of the two homologous chromosomes). They can be propagated as such and/or used to create transgenic animals. In such case, homozygous transgenic (with I-SpomI sites at equivalent positions in the two homologous chromosomes) can be constructed by regular methods such as mating. Homozygous cell lines can be isolated from such animals. Alternatively, homozygous cell lines can be constructed from heterozygous cell lines by secondary transformation with appropriate DNA constructs. It is also understood that cell lines containing compensated heterozygous I-SpomI insertions at nearby sites in the same gene or in neighboring genes are part of this invention.

Above mouse cells or equivalents from other vertebrates, including man, can be used. Cells from invertebrates can also be used. Any plant cells that can be maintained in culture can also be used independently of whether they have ability to regenerate or not, or whether or not they have given rise to fertile plants. The methods can also be used with transgenic animals.

2. Site Specific Gene Expression

Similar cell lines-can also be used to produce proteins, metabolites or other compounds of biological or biotechnological interest using a transgene, a variety of promoters, regulators and/or structural genes. The gene will be always inserted at the same localisation in the chromosome. In transgenic animals, it makes possible to test the effect of multiple drugs, ligands, or medical proteins in a tissue-specific manner.

3. The I-SpomI recognition site and I-SpomI enzyme can also be used in combination with homologous recombination techniques, such as that disclosed in EP 0419621B1. For example, insertion of the I-SpomI recognition site in the CF1R locus using homologous sequences flanking the CFTR gene in the genomic DNA can be done. The I-SpomI site can be inserted by spontaneous gene replacement by double-crossing over (Le Mouellic et al., *Proc. Natl. Acad. Sci. USA* 87: 4712-4716, 1990).

It is understood that the inserted sequences can be maintained in a heterozygous state or a homozygous state. In cases of transgenic animals with the inserted sequences in a heterozygous state, homozygation can be induced, for example, in a tissue specific manner, by induction of I-SpomI expression from an inducible promoter.

The insertion of the I-SpomI recognition site into the genome by spontaneous homologous recombination can be achieved by the introduction of a plasmid construct containing the I-SpomI recognition site and a sequence sharing homologies with a chromosomal sequence in the targeted cell The input plasmid is constructed recombinantly with a chromosomal targeted. This recombination leads to a site-directed insertion of at least one I-SpomI recognition site into the chromosome. The targeting construct can either be circular or linear and may contain one, two, or more parts of homologies With any sequence contained in the targeted cell. The targeting mechanism can occur either by the insertion of the plasmid construct into the target (O type vectors) or by the replacement of a chromosomal sequence by a sequence containing the I-SpomI recognition site (^L type vectors). See Valancius and Smithies, *Mol. Cell Biol.* 11: 4389-4397 (1991).

The chromosomal targeted locus can be exons, introns, promoter regions, locus control regions, pseudogenes, retroelements, repeated elements, non-functional DNA, telomers, and minisatellites. The targeting can occur at one locus or multiple loci, resulting in the insertion of one or more I-SpomI I sites into the cellular genome.

The use of embryonic stem cells for the introduction of the I-SpomI recognition sites into a precise locus of the genome allow, by the reimplantation of these cells into an early embryo (amorula or a blastocyst stage), the production of mutated mice containing the I-SpomI recognition site at a precise locus. These mice can be used to modify their genome in expressing the I-SpomI enzyme into their somatic cells or into their germ line.

4. Biomedical Applications

Various applications can be done with the sequences, cells, animals, chromosomes, and methods according to the invention.

One application is gene therapy. Specific examples of gene therapy include immunomodulation (i.e. changing range or expression of IL genes); replacement of defective genes; and excretion of proteins (i.e. expression of various secretory protein in organelles).

The present invention further embodies transgenic organisms, for example animals, where an I-SpomI restriction site is introduced into a locus of a genomic sequence or in a part of a cDNA corresponding to an exon of the gene. Any gene of a genome (animal, human, insect, or plant, etc.) in which an I-SpomI site is introduced can be targeted by a plasmid containing the sequence encoding the corresponding endonuclease. Introduction of the I-SpomI site may be accomplished by homologous recombination. Thus, any gene can be targeted to a specific location for expression.

Transgenic organisms can be used in screening methods.

Gene activation can be controlled by I-SpomI. For example, a I-SpomI recognition site can be introduced into transgenic mouse strains containing, under the control of the neuron specific enolase promoter (pNSE) (Forss-Petter et al., Neuron, 5:187-197 (1990)), a duplication of a part (e.g., 62 bp) of the nlsLacZ gene in tandem repeat, thus creating a loss of the function of the gene by the introduction of a stop codon into the open reading frame. The expression of the I-SpomI enzyme in these nice can reactivate the recombination between the two tandem repeats leading to the reactivating of the gene in all of the central nervous system (CNS). The same experiment can be realized with the DT-A fragment of the dyphteric toxin leading to the genetic ablation of the entire CNS. The genetic ablation can be performed by a tissue specific promoter or by the expression of the I-SpomI modified DT-A in a natural locus obtained by gene targeting.

It is possible to-activate a specific gene in vivo by I-SpomI induced recombination. The I-SpomI I cleavage site is introduced between a duplication of a gene in tandem repeats, creating a loss of function. Expression of the endonuclease I-SpomI can induce the cleavage between the two copies. The reparation by recombination is stimulated and results in a functional gene.

Specific translocation of chromosomes or deletion can be induced by I-SpomI cleavage. Locus insertion can be obtained by integration of one at a specific location in the chromosome by "classical gene replacement." The cleavage of recognition sequence by I-SpomI endonuclease can be repaired by non-lethal translocations or by deletion followed by end-joining. A deletion of a fragment of chromosome could also be obtained by insertion of two or more I-SpomI sites in flanking regions of a locus. The cleavage can be repaired by recombination and results in deletion of the complete region between the two sites.

I-SpomI, being part of an evolutionarily conserved family of proteins, it is understood that all applications developed with I-SpomI can also be made with other endonucleases provided that their cleavage specificity is high enough to be able to be recognized as a unique site in genomes of complex organisms such as fungi, animals, or plants. In some cases, the endonucleases can be directly expressed from their natural genes. In other cases, artificial genes need to be constructed due to the variability of the genetic code in the cell compartments in which such enzymes are naturally encoded. Constructions and all series of manipulations performed with I-SpomI and its site can be easily transformed with other endonucleases. Likewise, I-SpomI can be substituted in applications with other enzymes, such as I-SceI.

I-SpomI can be used in combination with other enzymes, such as I-SceI, I-CreI, I-CeuI, and I-DmoI. See, e.g., U.S. Pat. No. 5,474,896. For example, a recombinant chromosome or cell can be constructed containing one or more I-SpomI restriction site and one or more Group I intron encoded endonuclease site (e.g., I-SceI sites). In another embodiment, a transgenic mouse can be constructed containing one or more I-SpomI restriction site and one or more Group I intron encoded endonuclease site (e.g., I-SceI sites). The sites can be at the same or different chromosomal locations.

I-SpomI can be used in combination with other enzymes, such as I-SceI to promote in vivo recombination. For example, using an expression vector expressing I-SpomI and I-SceI, or two separate expression vectors expressing the enzymes, the expression of both of these enzymes can be introduced into cells. The expression of these enzymes allows double-stranded breaks to be introduced simultaneously or sequentially into different parts of a genome. This approach can be used, for example, to delete stretches of DNA or to facilitate multiple recombination events.

The entire disclosure of all references cited herein is hereby incorporated by reference.

Biological Deposits

A plasmid containing the polynucleotide encoding the ORF I-SpomI enzyme has been deposited at Collection Nationale de Cultures de Microorganismes (CNCM), 25, Rue du Docteur Roux, 75724 Paris, Cedex 15, France on Mar. 6, 2001, under accession number I-2643 (reference identification: *E. coli* BL21 (DE3) pLysS/pSP003).

The invention will be more completely understood with reference to the examples that follow.

EXAMPLE 1

Construction of Plasmids for Expression of I-SpomI and Activity Assays

Figure 1A:
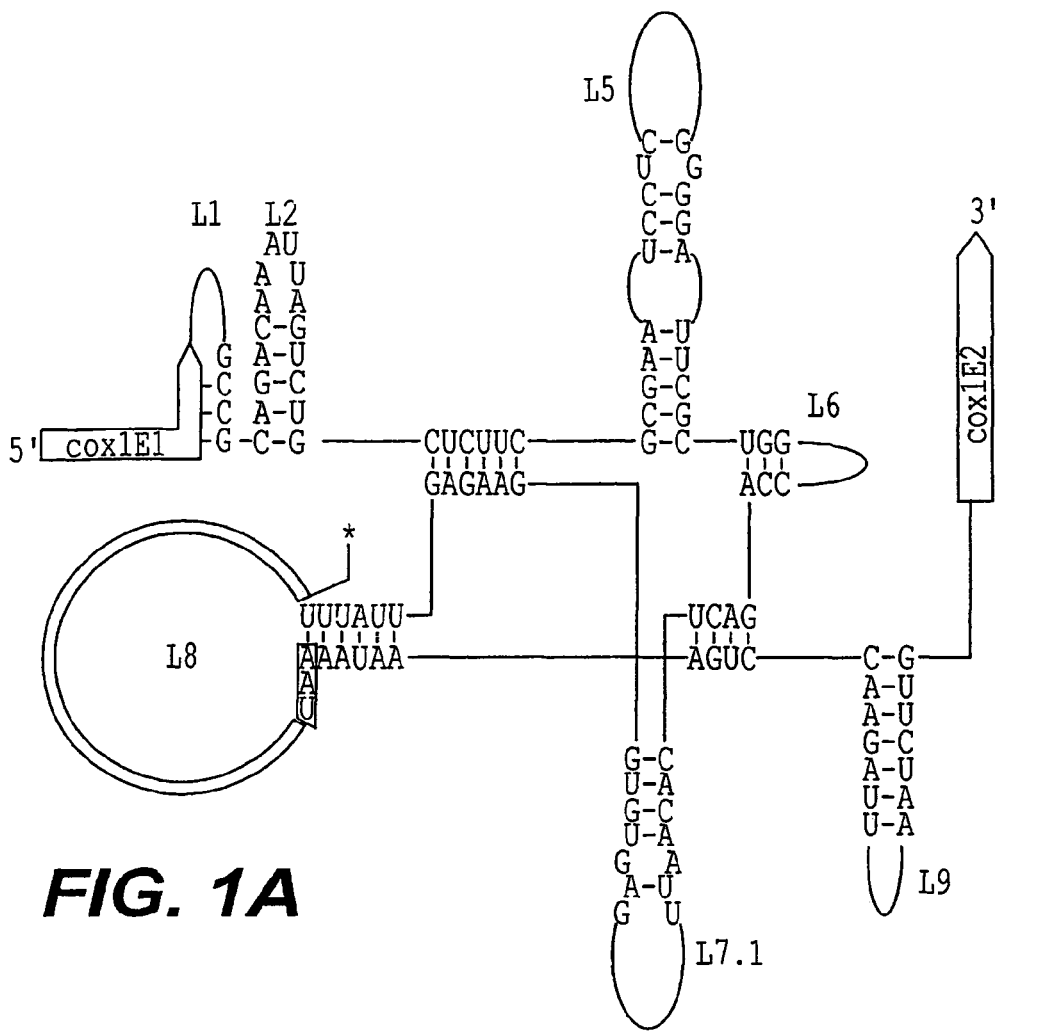
FIG. 1A. RNA secondary structure of cox1I1b intron of *Schizosaccharomyces pombe*. The nucleotides encoding the core of the endonuclease consisting of the two LAGLIDADG (SEQ ID NO: 17) motifs (P1 and P2) are located in loop 8 (L8). For the biochemical characterization of I-SpomI, a PCR-fragment including all codons of L8 was cloned into the expression vector pET16b. * represents the artificial start codon in primer SP003. The box at the end of the loop marks the stop codon. L2 sequence disclosed as SEQ ID NO: 13.

For the expression of I-SpomI in *E. coli* we cloned various PCR fragments amplified off *S. pombe* strain X39 genomic DNA (47) into expression vector pET16b (Novagen, Madison). The expressed protein is fused with a N-terminal 10× His-tag (SEQ ID NO: 18) to facilitate further purification. Three recombinant plasmids were constructed (FIG. 1): (i) Plasmid pSP001 contains a fragment of 520 codons corresponding to the entire open reading frame from the initiator ATG-codon in cox1E1 to the internal stop codon in cox1I1b (primer SP001m: 5'-GCACGCATGTCATATGGTCT-TGAGTTTAATGAACTCTTG-3' [SEQ ID NO:1], primer SP002m: 5'-GCGTAGATGGATCCAAGTGATACTTGAT-AGTGGTGG-3' [SEQ ID NO:2]). (ii) Plasmid pSP003 contains the shortest insert, covering the 304 codons located in loop 8 (FIG. 1A) of the intron secondary structure including the two LAGLIDADG-motifs (SEQ ID NO: 17) (primer SP003 5'-GAGAGCGCATATACATAT-GAATAAATTTTTTAATAGACATCC-3' [SEQ ID NO:3], together with primer SP002m). (iii) The third plasmid pSP005 was constructed using primer SP005 with primer SP002m giving a product of 386 codons covering the total sequence of the cox1I1b ORF (primer SP005: 5'-GCAT-AUAGGATCCATGTTAAAGCCGCAGACAAAATTG-3' [SEQ ID NO:4] together with primer SP002m). Each of the plasmids was transformed into expression host *E. coli* BL21 (DE3) pLysS (Novagen, Madison).

Plasmid pP3E5-2 (48) served as template to determine the I-SpomI cutting-site and for the activity tests. This derivative of pUC18 contains a cloned mtDNA fragment of the cox1 sequence from the intronless strain P3 (49).

To characterize the recognition site we generated a set of mutants of the region flanking the intron insertion site from the intronless gene by synthesis of oligonucleotides. Each mutant corresponds to a single transversion from position −13 to +12 nt around the intron insertion site. Annealed complementary oligonucleotides were cloned into pUC19 using the BamHI and HindIII sites. An additional EcoRV site was incorporated into the oligonucleotide sequence to screen proper recombinant molecules. Two independent clones of each ligation experiment were used in the tests to carry out the cleavage reactions in duplicate.

EXAMPLE 2

Expression and Purification of the Endonuclease

Recombinant proteins were expressed using the T7 expression system provided by Novagen, Madison. A preculture of the *E. coli* BL21 (DE3) pLysS, transformed with pSP003, was grown overnight at 37° C. in 50 ml LB medium with ampicillin (100 µg/ml) and chloramphenicol (34 µg/ml) and was then diluted 100-fold in 3 liters of fresh, prewarmed medium of the same composition. Cells were grown at 37° C. to an $OD_{600}$ of 0.6-0.8 before inducing the expression by adding isopropyl-β-D-thiogalactopyranoside (EPTG). After induction, the cells were grown for another three hours to an $OD_{600}$ of 2.3-2.8, harvested, washed with water and stored in aliquots at −70° C. For the purification, we harvested cells from 1 liter of main culture. Immediately before using the cells, pellets were thawed on ice and resuspended in 30 ml lysis buffer (30 mM HEPES pH8, 300 mM NaCl, 20 mM Imidazole) including protease inhibitors (Pefablock 1 µg/ml, Aprotinin 2 µg/ml. Leupeptin 0.5 µg/mL Pepstatin 1 µ/ml). All following purification steps were accomplished at 4° C. Disruption of the cells was performed by using a French press and subsequently the crude homogenate was centrifuged at 40000×g for 45 min in a Beckman JA25.50 rotor. The supernatant was immediately decanted and loaded onto the 1 ml HiTrap chelating affinity column (Amersham Pharmacia Biotech, Little Chalfont), charged with $Ni^{2+}$. Purification steps using the affinity column were carried out on an Äkta Purifier (Amersham Pharmacia Biotech, Little Chalfont) (FIG. 2). The elution buffer, in which the enzyme was present after the elution step was changed to 100 mM Diethanolamine pH9.0 by using Micro Bio-Spin size exclusion columns (Bio-Rad, Hercules). The protein was stored at −20° C. after adding glycerol to a final volume of 50% and the protein concentration was determined using the Bio-Rad Bradford protein assay (Bio-Rad, Hercules).

To document the purification and to identify the band of expressed I-SpomI, we took samples at different steps of the procedure and ran them on SDS-12% polyacrylamide gels. Afterwards they were transferred onto nitrocellulose membrane by using a semi-dry transfer cell (Bio-Rad, Hercules) according to (50). The membrane was incubated then for 1 h at 37° C. in TBST containing 2% milk powder (10 mM Tris-HCl at pH8.0, 150 mM NaCl, Tween 20 0.5% and 2% nonfat dried milk Afterwards, an antibody against the His-tag, coupled to horseraddish peroxidase was diluted in the TBST-milk solution 1:4500 and the membrane was incubated for 1 h at 37° C. Then it was washed two times with TBST and once with PBS (50). Detection of the BRP-activity was carried out following the manual of the ECL-Kit (Amersham Pharmacia Biotech, Little Chalfont). Different samples were taken before or after the induction with IPTG (the crude homogenate, the lysed cells, the supernatant after centrifugation, the flow-through of peak and non-peak fractions). A sample of each of the first 15 fractions was loaded on a SDS-12% polyacrylamide gel and stained with Coomassie brilliant blue R250 to identify the fraction with the best ratio of expressed enzyme relative to other present proteins.

Figure 1B:
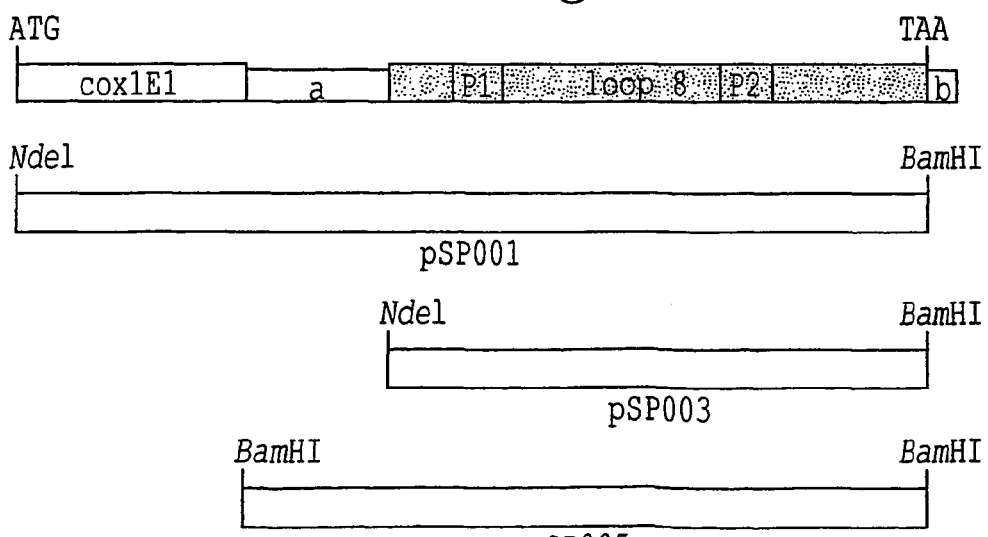
FIG. 1B. Cloned fragments of the I-SpomI reading frame. The top scheme symbolizes the entire sequence of the first exon (cox1E1) and the intron in the cox1 gene of *S. pombe*. grey: The exon cox1E1 with the native start codon ATG. dark grey: 912 nt of the 1560 nt of the entire ORF are located in the region that builds up L8 on the RNA level, black: coding sequence for the LAGLIDADG (SEQ ID NO: 17) motifs. light grey: Sequences for the loops 1 to 7 are located in region a. white: The sequence non-coding region downstream to the TAA stop codon is located in loop L9.

From previous experiments showing the homing of intron cox1I1b in crosses (47, 48), the product of the intron cox1I1b was suspected to have endonuclease activity. As it was unclear whether the entire reading frame including the exon-part is essential for a functional protein we expressed the entire ORF comprising intron and exon sequence, or simply the whole intron and a region corresponding to loop 8 of the RNA secondary structure (FIG. 1). Contrary to most other cases in which the reading frame of mitochondrial introns is translated using non-universal code, this intron ORF does not contain any UGA codon (45). Thus it was not necessary to change any nucleotides in the sequence of the gene.

Expression was assayed in *E. coli* in time course experiments and it was found that the best expression of the gene product of the smallest ORF was 3 h after induction (data not shown). Thus we decided to proceed with the expression plasmid called pSP003. The soluble fraction after cell lysis contains the endonucleolytic activity (as will be shown later). In this fraction we found two major bands which were also detectable in a Western blot experiment using a His-tag antibody. The size of the stronger band is in accordance with the expected molecular weight of the fusion gene-product (38.7 kDa), accompanied by a weaker band of about 30 kDa size as a possible degradation product (FIG. 2B, C). A typical elution profile from a single purification step on a Ni-column is shown in FIG. 2A. The protein peak always coelutes with a strong nucleic acid signal. The Bradford assay displayed a total protein concentration of 0.3 µg/µl. With the major protein band at 38.7 kDa corresponding to about one third of the total, the concentration of I-SpomI could be estimated at circa 0.1 µg/µl. The preparation was stored in 100 mM Diethanolamine pH9.0/50% glycerol at −20° C. and it was shown that these conditions kept the endonuclease activity stable for several months.

EXAMPLE 3

Determination of the I-SpomI Cutting-site

Determination of the cleavage pattern of I-SpomI was carried out with a short PCR product including the expected homing site at the junction of the sequences of exons cox1E1 and cox1E2. The primer of the sense strand SP009 (5'-CTAGAGTAAATAATTTCACATTC-3' [SEQ ID NO:5]) annealed at position −100 relative to the intron insertion site. Primers SP008 (5'-ATGCAAATAATGGCATTTGATAT-3' [SEQ ID NO:6]) and SP010 (5'-AATTTACTGATCCTAAT-GTTGAT-3' [SEQ ID NO:7]) of the complementary strand hybridised +173 nt respectively +129 nt downstream (FIG. 3A). Plasmid pP3E5-2 (48), linearized with PstI, served as template for PCR to prepare DNA material to determine the cleavage site. The material was treated with Shrimp Alkaline Phosphatase and Exonuclease I to remove excess nucleotides and primers and then denatured. Prepared like this, the PCR-product was used as template to generate a DNA sequencing ladder using cycle sequencing (Thermo Sequenase Cycle Sequencing Kit, USB, Miles Road) and 5'-end-labeled primer SP009 or SP008/SP010. 5'-end-labeled primers were also used to produce single end-labeled substrate for I-SpomI by PCR-amplification of plasmid pP3ES-2 (48) as template. Before cleavage, DNA fragments were purified from non-incorporated deoxynucleotides and radioactive oligonucleotides via an Amicon Microcon PCR centrifugal filter device (Millipore, Bedford) according to the manual, followed by phenol-extraction and precipitation. Finally, the PCR-products were resuspended in 15 µl of water. Digestion with I-SpomI was performed in a total reaction volume of 25 µl (6 µl endonuclease preparation, 100 mM Diethanolamine, pH9.0, 2.5 mM MgCl$_2$, 1 µl of dissolved PCR product.) at 37° C. for 10 min. The reaction was terminated by the addition of 0.1 volumes of a 10× stop solution (0.1 M Tris-HCl pH7.5, 0.25M EDTA, 5% SDS, 0.5 mg/ml Proteinase K according to (51)) and incubated for 15 min to 50° C., and for 3 min up to 95° C. to inactivate the Proteinase K. Proteinase K was removed by phenol extraction and the sample precipitated. An undigested sample was treated in the absence of I-SpomI as control. After the endonuclease digestion we ran the PCR-products alongside the DNA sequencing reactions. All samples were denatured after addition of stop solution delivered with the Sequenase kit at 75° C. for 2 min and separated on a 6% polyacrylamide/50% urea gel. Subsequently the gel was dried and exposed to an autoradiography film or a Phosphor Imager screen (Molecular Dynamics, Sunnyvale) over night at respectively −70° C. or at 25° C. Evaluation of the results was performed with Image Quant 5.0 Software.

The cleavage pattern of I-SpomI was determined by using 5'-end labeled PCR-products corresponding to the region flanking the intron insertion site in the continuous, sequence of the cox1-gene of *S. pombe* strain P3 (44) as described under Materials and Methods. DNA was digested with I-SpomI and separated on a sequencing gel (FIG. 3). Each DNA-strand shows a strong signal after cleavage with I-SpomI which is absent from uncleaved DNA. The cut position could be localized precisely by comparison with the sequencing ladder of the same DNA fragment. According to this, a cut takes place 2 bp downstream of the intron insertion site on the sense strand and 2 bp for the lower strand generating 3'-overhangs of 4 nt. This cleavage pattern is well known from other homing endonucleases. It has been reported for members of the dodecapeptide family like I-CreI (17), I-SceI (16) and II (37), I-CeuI (30) and I-DmoI (20) as well as for the His-Cys Box/ ββα-Me protein I-PpoI (53).

EXAMPLE 4

Activity Test

Substrates for I-SpomI were obtained by a PCR with primer SP009 and radioactive labeled primer SP008 as described in the preceding paragraph. Standard conditions for the endonuclease cut were 100 mM Diethanolamine at pH9.0, 5 mM MgCl$_2$, 100 mM NaCl, 1 µl of purified PCR-product in 15 µl water and finally 5 µl of prepared endonuclease in a total volume of 25 µl. The reactions were incubated at 37° C. for 20 min MgCl$_2$ concentrations varied from 1 mM up to 40 mM, NaCl varied from 0 mM up to 200 mM. The influence of temperature was monitored between 25° C. to 65° C. Tested pH-values ranged from pH6.0 (30 mM MES), pH7.0, pH8.0 (100 mM HEPES) and from pH9.0 to 10.0 (100 mM Diethanolamine). Reactions were stopped as mentioned before. They were separated on a 5% polyacrylamide/50% urea gel.

After the run, the gel was soaked in a solution of 10% acetic acid/20% ethanol, put on Whatman 3MM paper (Whatman, Maidstone) and dried. A Phosphor Imager screen (Molecular Dynamics, Sunnyvale) was exposed to the dried gel for 2.5 h at 25° C., results were quantified with the software mentioned before.

Known parameters that influence the activity of other homing endonucleases are the concentration of monovalent ($Na^+$ and $K^+$) and divalent cations ($M^{2+}$ and $Mn^{2+}$), temperature and proton concentration of the solution. In order to determine the optimal conditions for activity of I-SpomI we use a PCR-product ranging from position −100 bp (SP009) to +173 bp (SP008) relative to the intron insertion site (FIG. 3A) as substrate for the I-SpomI endonuclease activity assay. For the assay, one of the primers was 5'-endlabeled with $[\gamma-^{32}P]$-ATP. A cleavage by I-SpomI should generate a smaller detectable band of 173 bp in length. We found that $M^{2+}$ is essential for the cutting capacity of I-SpomI as previously reported for all other known homing endonucleases. In the absence of $Mg^{2+}$, no activity is detectable (not shown). Optimal $Mg^{2+}$ concentration ranges from 5 mM to 7.5 mM (FIG. 4A). Lower or higher concentrations are disadvantageous for the enzyme activity. I-SpomI needs $Na^+$ but the tolerated concentration range is broad (FIG. 4B). Cleavage of the substrate at different temperatures between 25° C. and 65° C. indicated a clear optimum at 42° C. (FIG. 4C). At temperatures of 30° C. and lower, we found almost no activity. I-SpomI is active up to 65° C. The influence of the proton concentration clearly showed a preference of I-SpomI for alkaline pH-conditions (FIG. 4D). At pH-values between 6.0 to 8.0 the amount of cleaved DNA stayed on a low level of about 30% but at pH9.0 and higher it was raised to 85% of cleavage.

For I-ScaI (43) optimal cleavage conditions have been reported as follows: $Mg^{2+}$ 8 mM, $Na^+$ about 50 mM, temperature between 28° C. and 40° C., pH between 8.5 and 9.0. The preference for high temperatures and alkaline pH-values strongly resembles I-SceI (29) and III (54), both expressed in bacteria I-SceII (19), extracted out of yeast mitochondria in contrast, prefers a neutral pH and a temperature around 30° C.

EXAMPLE 5

Determination of the Recognition Sequence

As described before, we used plasmids containing the nucleotide sequence from position −13 to +12 around the insertion site of intron cox1I1b (see FIG. 5A). Complementary oligonucleotides were annealed in NEBuffer2 (New England Biolabs, Beverly) after denaturing the mix for 3 min at 95° C. and cooling it down slowly to 4° C. They were cloned into BamHI/HindIII-digested pUC19. The recombinant plasmids were transformed via electroporation in E. coli strain DH10B and afterwards checked by EcoRV/XmnI-digestion of alkaline plasmid preparations (50). DNA of recombinant plasmids was prepared from cultures of 40 ml LBA according to the QIAfilter tip 100 protocol (QIAGEN, Hilden). The concentration of the prepared plasmids was adjusted to 0.3 µg/µl. Before exposing the plasmids to I-SpomI, they were digested with NdeI and AlwNI for 3 h at 37° C., subsequently treated for 20 min at 65° C., precipitated and dissolved in water to a final concentration of 0.1 µg/ml. The I-SpomI-digest was carried out in a volume of 50 µl (250 ng DNA, 100 mM Diethanolamine pH9.6, 5 mM $MgCl_2$, 100 mM NaCl, 5 µl I-SpomI). The digestion was terminated by adding 0.1 volumes stop solution (0.1M Tris-HCl pH7.5, 0.25M EDTA, 5% SDS) and incubating for 3 min at 65° C., followed by phenol-extraction and precipitation. Digested products were resuspended in 10 µl water and separated on a 0.8% agarose gel. The gel was stained with 0.5 µg/µl ethidium bromide after the run and the DNA was transferred via vacuum blot onto a Hybond-$N^+$ nylon membrane (Amersham Pharmacia Biotech, Little Chalfont). After transfer, the membrane was prehybridised for 1.5 h at 65° C. in hybridization buffer (0.25M phosphate buffer, 7% SDS, 1 mM EDTA, 1% BSA) and then hybridised overnight with random labeled pUC19 as probe (52). Incorporation of the label was determined in a 1 µl aliquot of the final probe preparation in a scintillation counter. After hybridization, the buffer containing the probe was removed, the membrane was washed with hybridization buffer at 65° C. and exposed to a Phosphor Imager screen (Molecular Dynamics, Sunnyvale) for 2.5 h at 25° C. and results were documented as mentioned before.

In order to determine the extent of the recognition site of I-SpomI we have synthesized mutated sequences by introducing one transversion at a time in a −13 to +12 region flanking the intron insertion site. This was done by synthesizing mutant alleles as described in Materials and Methods. Digestion of the plasmids with NdeI and AlwNI results in two bands of 1652 bp and 1041 bp respectively, the smallest one containing the I-SpomI cleavage site. Digestion of this fragment by I-SpomI generates two bands of 801 bp and 240 bp, shown in FIG. 5A. Results of cutting experiments with the different mutants are summarized in the boxes "Cut" and "%" in FIG. 5A. Nucleotides at positions −11, −10, −8 to −4, +2 to +6, +8 and +9 are essential for substrate recognition by I-SpomI. Transversion of the nucleotides at positions −4 and +2 almost completely abolishes the cleavage. Changes in some nucleotides in the middle positions −3 to +1, and at the borders of the sequence, positions −9 and +7, have no effect on the recognition event. Thus the extent of the site is 20 bp in total. Within these 20 nucleotides, only 14 are essential for I-SpomI specificity.

REFERENCES

1. Dujon, B. (1989) *Gene,* 82,91-114.
2. Lambowitz, A. M. and Belfort, M. (1993) *Annu Rev Biochem,* 62, 5 87-622.
3. Belfort, M. and Roberts, R. J. (1997) *Nucleic Acids Res,* 25, 3379-3388.
4. Jurica, M. S. and Stoddard, B. L. (1999) *Cell Mol Life Sci,* 55, 1304-1326.
5. Kennell, J. C., Moran, J. V., Perlman, P. S., Butow, R. A. and Lambowitz, A. M. (1993) *Cell,* 73, 133-146.
6. Zimmerly, S., Guo, H., Eskes, R., Yang, J., Perlman, P. S. and Lambowitz, A. M. (1995) *Cell.* 83, 529-538.
7. Guo, H., Zimmerly, S., Perlman, P. S. and Lambowitz, A. M. (1997) *Embo J.* 16, 6835-6848.
8. Kane, P. M., Yamashiro, C. T., Wolczyk, D. F., Neff, N., Goebl, M. and Stevens, T. H. (1990) *Science,* 250, 651-657.
9. Shub, D. A. and Goodrich-Blair, H. (1992) *Cell,* 71, 183-186.
10. Dalgaard, J. Z., Klar, A. J., Moser, M. J., Holley, W. R., Chatterjee, A. and Mian, I. S. (1997) *Nucleic Acids Res,* 25, 4626-4638.
11. Pietrokovski, S. (1998) *Protein Sci,* 7, 64-71.
12. Perler, F. B. (1998) *Cell,* 92, 1-4.
13. Derbyshire, V., Wood, D. W., Wu, W., Danscreau, J. T., Dalgaard, J. Z. and Belfort, M. (1997) *Proc Natl Acad Sci USA,* 94, 11466-11471.
14. Hu, D., Crist, M., Duan, X., Quiocho, F. A. and Gimble, F. S. (2000) *J Biol Chem,* 275, 2705-2712.
15. Ichiyanagi, K, Ishino, Y., Ariyoshi, M., Komori, K and Morikawa, K (2000) *J Mol Biol,* 300, 889-901.

16. Colleaux, L., D'Auriol, L., Galibert, F. and Dujon, B. (1988) *Proc Natl Acad Sci USA,* 85, 6022-6026.
17. Thompson, A. J., Yuan, X., Kudlicki, W. and Herrin, D. L. (1992) *Gene,* 119, 247-251.
18. Dalgaard, J. Z., Garrett, R. A. and Belfort, M. (1994) *J Biol Chem,* 269, 28885-28892.
19. Wernette, C. M., Saldahna, R., Perlman, P. S. and Butow, R. A. (1990) *J Biol Chem,* 265, 18976-18982.
20. Dalgaard, J. Z., Garrett, R. A. and Belfort, M. (1993) *Proc Natl Acad Sci USA,* 90, 5414-5417.
21. Heath, P. J., Stephens, K. M., Monnat, R. J., Jr. and Stoddard, B. L. (1997) *Nat Struct Biol,* 4, 468-476.
22. Duan, X., Gimble, F. S. and Quiocho, F. A. (1997) *Cell,* 89, 555-564.
23. Silva, G. H., Dalgaard, J. Z., Belfort, M. and Van Roey, P. (1999) *J Mol Biol,* 286, 1123-1136.
24. Flick, K. E., Jurica, M. S., Monnat, R. J., Jr. and Stoddard, B. L. (1998) *Nature,* 394, 96-101.
25. Wittmayer, P. K. and Raines, R. T. (1996) *Biochemistry,* 35, 1076-1083.
26. Pingoud, A. and Jeltsch, A. (1997) *Eur J Biochem.* 246, 1-22.
27. Kuhlmann, U. C., Moore, G. R., James, R., Kleanthous, C. and Hemmings, A. M. (1999) *FEBS Lett,* 463, 1-2.
28. Wernette, C. M. (1998) Biochem Biophys Res Commun, 248, 127-133.
29. Monteilhet, C., Perrin, A., Thierry, A., Colleaux, L. and Dujon, B. (1990) Nucleic Acids Res, 18, 1407-1413.
30. Marshall, P. and Lemieux, C. (1991) Gene, 104, 241-245.
31. Lykke-Andersen, J., Garrett, R-A. and Kjerns, J. (1996) Nucleic Acids Res, 24, 3982-3989.
32. Lazowska, J., Jacq, C. and Slonimski, P. P. (1980) Cell, 22, 333-348.
33. De La Salle, H., Jacq, C. and Slonimski, P. P. (1982) Cell, 28, 721-732.
34. Lambowitz, A. M. and Perlman, P. S. (1990) Trends Biochem Sci, 15, 440-444.
35. Weeks, K. M. and Cech, T. R. (1996) Science, 271, 345-348.
36. Dujardin, G., Jacq, C. and Slonimski, P. P. (1982) Nature, 298, 628-632.
37. Wenzlau, J. M., Saldanha, R-J., Butow, R. A. and Perlman, P. S. (1989) Cell, 56, 421-430.
38. Szczepanek, T., Jamoussi, K. and Lazowska, J. (2000) Mol Gen Genet, 264, 137-144.
39. Ho, Y., Kim, S J. and Waring, R. B. (1997) Proc Natl Acad Sci USA, 94, 8994-8999.
40. Ho, Y. and Waring, R. B. (1999) J Mol Biol, 292, 987-1001.
41. Lazowska, J., Szczepanek, T., Macadre, C. and Dokova, M. (1992) C R Acad Sci III, 315, 37-41.
42. Szczepanek, T. and Lazowska, J. (1996) Embo J, 15, 3758-3767.
43. Monteilhet, C., Dziadkowiec, D., Szczepanek, T. and Lazowska, J. (2000) Nucleic Acids Res, 28, 1245-1251.
44. Schafer, B., Merlos-Lange, A. M., Anderl, C., Welser, F., Zimmer, M. and Wolf, K. (1991) *Mol Gen Genet,* 225, 158-167.
45. Lang, B. F., Ahne, F., Distler, S., Trinkl, H., Kaudewitz, F. and Wolf, K. (1983) Mitochondria 1983. Walter de Gruyter, Berlin-NY.
46. Lang, B. F. (1984) Embo J, 3, 2129-2136.
47. Schafer, B., Wilde, B., Massardo, D. R., Manna, F., Del Giudice, L. and Wolf, K. (1994) Curr Genet, 25, 336-341.
48. Schafer, B. and Wolf, K. (1997) In Schenk, H. E. A, Herrmann, R. G., Jeon, K. W., Mfiller, N. E. and Schwemmler, W. (eds.), Eukaryotism and Symbiosis: Intertaxonic combination versus symbiotic adaptation Springer-Verlag, Berlin, Heidelberg, New York, pp. 139-144.
49. Merlos-Lange, A. M., Kanbay, F., Zimmer, M. and Wolf, K. (1987) Mol Gen Genet, 206, 273-278.
50. Sambrook, J., Fritsch, E. F. and Maniatis, T. (1989) *Molecular Cloning: a laboratory manual.* 2nd ed. Cold Spring Harbor Laboratory Press, Cold Spring Harbor, N.Y.
51. Wang, J., Kim, H. H., Yuan, X. and Herrin, D. L. (1997) *Nucleic Acids Res,* 25, 3767-3776.
52. Wolff, R. and Gemmill, R. (1997) In Birren, B., Green, E. D., Klapholz, S., Myers, R. M. and Roskams, J. (eds.), *Genome analysis—A laboratory manual.* 1 ed. Cold Spring Harbor Laboratory Press, Cold Spring Harbor, N.Y., Vol. 1, pp. 60-61.
53. Muscarella, D. E., Ellison, E. L., Ruoff, B. M. and Vogt, V. M. (1990) *Mol Cell Biol,* 10, 3386-3396.
54. Schapira, M., Desdouets, C., Jacq, C. and Perea, J. (1993) *Nucleic Acids Res,* 21, 3683-3689.
55. Guo, W. W., Moran, J. V., Hoffman, P. W., Henke, R. M., Butow, R-A. and Perlman, P. S. (1995) *J Biol Chem,* 270, 15563-15570.
56. Perea, J., Desdouets, C., Schapira, M. and Jacq, C. (1993) *Nucleic Acids Res,* 21, 358.
57. Cote, V., Mercier, J. P., Lemieux, C. and Turmel, M. (1993) *Gene,* 129, 69-76.
58. Turmel, M., Mercier, J. P., Cote, V., Otis, C. and Lemieux, C. (1995) *Nucleic Acids Res,* 23, 2519-2525.
59. Lykke-Andersen, J., Thi-Ngoc, H. P. and Garrett, R. A. (1994) *Nucleic Acids Res,* 22, 4583-4590.
60. Gimble, F. S. and Thorner, J. (1992) *Nature,* 357, 301-306.
61. Saves, I., Eleaume, H., Dietrich, J. and Masson, J. M. (2000) *Nucleic Acids Res,* 28, 4391-4396.
62. Perler, F. B., Comb, D. G., Jack, W. E., Mora, L. S., Qiang, B., Kucera, R. B., Benner, J., Slatko, B. E., Nwankwo, D. O., Hempstead, S. K. et al. (1992) *Proc Natl Acad Sci USA,* 89, 5577-5581.
63. Saves, I., Ozanne, V., Dietrich, J. and Masson, J. M. (2000) *J Biol Chem,* 275, 2335-2341.
64. Kostriken, R., Strathern, I N., Klar, A. J., Hicks, J. B. and Heffron, F. (1983) *Cell,* 35, 167-174.
65. Argast, G. M., Stephens, K. M., Emond, M. J. and Monnat, R. J., Jr. (1998) *J Mol Biol,* 280, 345-353.
66 Jurica, M. S., Monnat, R. J., Jr. and Stoddard, B. L. (1998) *Mol Cell,* 2, 469-476.
67. Gimble, F. S. and Wang, J. (1996) *J Mol Biol,* 263, 163-180.
68. Perlman, P. S. and Butow, R. A. (1989) *Science,* 246, 1106-1109.
69. Lambowitz, A. M. (1989) *Cell,* 56, 323-326.
70. Belfort, M. (1990) *Annu Rev Genet,* 24, 363-385.
71. Ogawa, S., Matsuo, K., Angata, K., Yanagisawa, K. and Tanaka, Y. (1997) *Curr Genet,* 31, 80-88.
72. Loizos, N., Tillier, E. R. and Belfort, M. (1994) *Proc Natl Acad Sci USA,* 91, 11983-11987.
73. Bell-Pedersen, D., Quirk, S., Clyman, J. and Belfort, M. (1990) *Nucleic Acids Res,* 18, 3763-3770.
74. Michel, F. and Westhof, E. (1990) *J Mol Biol,* 216, 585-610.
75. Rochaix, J. D., Rahire, M. and Michel, F. (1985) *Nucleic Acids Res,* 13, 975-984.
76. Ogawa, S., Naito, K., Angata, K., Morio, T., Urushihara, H. and Tanaka, Y. (1997) *Gene,* 191, 115-121.
77. Henke, R. M., Butow, R. A. and Perhnan, P. S. (1995) *Embo J,* 14, 5094-5099.

We claim:

1. The plasmid deposited at CNCM under accession number I-2643.

2. An isolated DNA sequence that encodes a polypeptide having I-SpomI endonuclease activity, wherein said DNA sequence consists of a nucleotide sequence that encodes the amino acid sequence of SEQ ID NO:12.

3. An isolated RNA fully complementary to the nucleotide sequence of claim 2.

4. The isolated DNA sequence of claim 2, wherein said nucleotide sequence that encodes the amino acid sequence of SEQ ID NO:12 is the nucleotide sequence of SEQ ID NO:9.

5. An expression vector comprising a DNA sequence that encodes a polypeptide having I-SpomI endonuclease activity, wherein said DNA sequence consists of a nucleotide sequence that encodes the amino acid sequence of SEQ ID NO:12, and wherein said expression vector is capable of directing expression of said polypeptide having I-SpomI endonuclease activity.

6. The vector of claim 5, wherein said vector is capable of directing expression of said polypeptide having I-SpomI endonuclease activity in mammalian cells.

7. The vector of claim 6, wherein said vector is an adenovirus vector.

8. The vector of claim 5, wherein said vector expresses said enzyme in insect cells.

9. The expression vector of claim 5, wherein said nucleotide sequence that encodes the amino acid sequence of SEQ ID NO:12 is the nucleotide sequence of SEQ ID NO:9.

10. A recombinant chromosome comprising a DNA sequence that encodes a polypeptide having I-SpomI endonuclease activity, wherein said DNA sequence consists of a nucleotide sequence that encodes the amino acid sequence of SEQ ID NO:12, and wherein said recombinant chromosome is capable of directing expression of said polypeptide having I-SpomI endonuclease activity.

11. The recombinant chromosome of claim 10, wherein said chromosome is from a eukaryotic or prokaryotic organism.

12. The recombinant chromosome of claim 11, wherein said chromosome is from a mammalian, insect, fungal, plant, yeast, bacterial, or nematode organism.

13. The recombinant chromosome of claim 10, wherein said nucleotide sequence that encodes the amino acid sequence of SEQ ID NO:12 is the nucleotide sequence of SEQ ID NO:9.

14. A recombinant cell comprising nucleic acid comprising a DNA sequence that encodes a polypeptide having I-SpomI endonuclease activity, wherein said DNA sequence consists of a nucleotide sequence that encodes the amino acid sequence of SEQ ID NO:12, and wherein said nucleic acid is capable of directing expression of said polypeptide having I-SpomI endonuclease activity.

15. The recombinant cell of claim 14, wherein said cell is from a eukaryotic or prokaryotic organism.

16. The recombinant cell of claim 14, wherein said cell is from a mammalian, insect, fungal, plant, yeast, bacterial, or nematode organism.

17. The recombinant cell of claim 14, wherein said nucleotide sequence that encodes the amino acid sequence of SEQ ID NO:12 is the nucleotide sequence of SEQ ID NO:9.

18. A non-human transgenic organism comprising a nucleic acid comprising a DNA sequence that encodes a polypeptide having I-SpomI endonuclease activity, wherein said DNA sequence consists of a nucleotide sequence that encodes the amino acid sequence of SEQ ID NO:12, and wherein said nucleic acid is capable of directing expression of said polypeptide having I-SpomI endonuclease activity.

19. The non-human transgenic organism of claim 18, wherein said organism is a mammalian, insect, fungal, plant, yeast, bacterial, or nematode organism.

20. The non-human transgenic organism of claim 18, wherein said nucleotide sequence that encodes the amino acid sequence of SEQ ID NO:12 is the nucleotide sequence of SEQ ID NO:9.

* * * * *

SEQUENCE LISTING

<160> NUMBER OF SEQ ID NOS: 18

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcacgcatgt catatggtct tgagtttaat gaactcttg                           39

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgtagatgg atccaagtga tacttgatag tggtgg                              36

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagagcgcat atacatatga ataaatttt taatagacat cc                        42

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcatattagg atccatgtta aagccgcaga caaaattg                            38

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctagagtaaa taatttcaca ttc                                            23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
atgcaaataa tggcatttga tat                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatttactga tcctaatgtt gat                                              23

<210> SEQ ID NO 8
<211> LENGTH: 1561
<212> TYPE: DNA
<213> ORGANISM: Schizosaccharomyces pombe

<400> SEQUENCE: 8
atgaactctt ggtggactta tgttaataga tggatattct caactaatgc taaggatatt      60
gccatactat atttattatt cggattggta tctgggataa ttggatctgt attctctttt     120
ataattagaa tggaactatc agctccagga tctcaattcc tttctggaaa tggtcaatta     180
tacaatgttg caatctcagc acatggtata cttatgattt tttcttcatt attcctgctt     240
tatttggtgc atttggtaat tatttagtac ctcttatgat aggtgctcca gatgttgctt     300
accctagagt aaataatttc acattctggt tactacctcc tgctctaatg ctattattaa     360
tttctgcatt aacagaagaa ggacctggtg gtggttggac ggttttaaag ccgcagacaa     420
aattgtctga aaactcttct cgatgcgaaa aagtcctcta ctcggaagta attactcagt     480
taatttattt tttaactagt aaaaagatta ctaacttggg gaaaattcgc ctggttaaat     540
ccatcagaga ctcgtttcta tcacaattag aaaataaaaa atgtttcttt ttggtttata     600
gaacaacata ctctttcgga gtgtgtttaa tgaagaggtt cttatttaat aaattttta     660 atagacatcc ttttacaagg gtaaaaagct gttttcatc atcttcacca tcaaaattct     720
cttttactca atggttagtt aggatttact gatggtgatg gttgttttag tatttcaaaa     780
caaaaaataa aaaatggcaa aaataaatgg tctcttactt taaattaac acaaaatctt     840 tataattata gaattttata ttttattaag agaaatttag gtattggttc actttataaa     900
gaatcttcaa ctaatacagt aatatatata gattaagaag aagagagcat cttaaaaga     960 ttatagatat ttttgatcaa ttccctcttt taactaaaaa atattgggat tattatttgt    1020 ttaaaaagc attccttaatt ttagaggacg ctaatctaaa ttcttttgaa aaaatagta    1080 aactagaaga gatcagaata gagaaaaagt ctttaaaaca atattctcca gttaatttag    1140 aaaaatatt aacaaagtct tggttaattg gatttattga agcagaaggg agcttttatt    1200
tactacaaaa aagccctgta agaataattc atgggttga gattactcaa aattatgaac    1260 aaccccctact tgctcagatt tcagagttcc tatttaattc tcaaatctca ccaaaaataa    1320
aatcaaaaaa aattccttaa ttacaaatta ttccttatca actagttcaa aagaaagaat    1380
gttatttctt tcatcttatt ttgaaaattg ttttaaagga gtaaaatcat tagaatttaa    1440
aatttggtct agatctttac gtaaaaatta taattttgaa cagcttttaa gagctagaga    1500
tttaattaga aaattaaaaa ataaatattc ccgaggatca caacatccaa aggataaata    1560
a                                                                     1561
```

<210> SEQ ID NO 9
<211> LENGTH: 919
<212> TYPE: DNA
<213> ORGANISM: Schizosaccharomyces pombe

<400> SEQUENCE: 9

| | | |
|---|---|---|
| atgaataaat tttttaatag acatcctttt acaagggtaa aaagctgttt ttcatcatct | 60 |
| tcaccatcaa aattctcttt tactcaatgg ttagtaggat ttactgatgg tgatggttgt | 120 |
| tttagtattt caaaacaaaa aataaaaaat ggcaaaaata aatggtctct acttttaaa | 180 |
| ttaacacaaa atctttataa ttatagaatt ttatatttta ttaagagaaa tttaggtatt | 240 |
| ggttcacttt ataaagaatc ttcaactaat acagtaatat atagattaag aagaagagag | 300 |
| catcttaaaa agattataga tatttttgat caattccctc ttttaactaa aaaatattgg | 360 |
| gattattatt tgtttaaaaa agcattctta attttagagg acgctaatct aaattctttt | 420 |
| gaaaaaaata gtaaactaga agagatcaga ataatagaga aaaagtcttt aaaacaatat | 480 |
| tctccagtta atttagaaaa atatttaaca aagtcttggt taattggatt tattgaagca | 540 |
| gaagggagct tttatttact acaaaaaaag ccctgtaaga ataattcatg ggtttgagat | 600 |
| tactcaaaat tatgaacaac ccctacttgc tcagatttca gagttcctat ttaattctca | 660 |
| aatctcacca aaaataaaat caaaaaaaaa ttccttaatt acaaattatt ccttatcaac | 720 |
| tagttcaaaa gaaagaatgt tatttctttc atcttatttt gaaaattgtt ttaaaggagt | 780 |
| aaaatcatta gaatttaaaa tttggtctag atctttacgt aaaaattata attttgaaca | 840 |
| gcttttaaga gctagagatt taattagaaa attaaaaaat aaatattccc gaggatcaca | 900 |
| acatccaaag gataaataa | 919 |

<210> SEQ ID NO 10
<211> LENGTH: 40
<212> TYPE: DNA
<213> ORGANISM: Schizosaccharomyces pombe

<400> SEQUENCE: 10
acctggtggt ggttggacgg tatatccacc actatcaagt        40

<210> SEQ ID NO 11
<211> LENGTH: 517
<212> TYPE: PRT
<213> ORGANISM: Schizosaccharomyces pombe

<400> SEQUENCE: 11

Met Asn Ser Trp Trp Thr Tyr Val Asn Arg Trp Met Phe Ser Thr Asn
 1               5                  10                  15

Ala Lys Asp Ile Ala Met Thr Tyr Leu Leu Phe Gly Leu Val Ser Gly
            20                  25                  30

Met Ile Gly Ser Val Phe Ser Phe Met Ile Arg Met Glu Thr Ser Ala
        35                  40                  45

Pro Gly Ser Gln Phe Thr Ser Gly Asn Gly Gln Leu Tyr Asn Val Ala
    50                  55                  60

Ile Ser Ala His Gly Met Thr Met Ile Phe Phe Ile Ile Pro Ala
65                  70                  75                  80

Leu Phe Gly Ala Phe Gly Asn Tyr Leu Val Pro Thr Met Met Gly Ala
                85                  90                  95

Pro Asp Val Ala Tyr Pro Arg Val Asn Asn Phe Thr Phe Trp Leu Thr
            100                 105                 110

Pro Pro Ala Thr Met Thr Leu Leu Ile Ser Ala Leu Thr Glu Glu Gly

```
              115                 120                 125
Pro Gly Gly Gly Trp Thr Val Leu Lys Pro Gln Thr Lys Leu Ser Glu
        130                 135                 140
Asn Ser Ser Arg Cys Glu Lys Val Thr Tyr Ser Glu Val Ile Thr Gln
145                 150                 155                 160
Leu Ile Tyr Phe Leu Thr Ser Lys Lys Ile Thr Asn Leu Gly Lys Ile
                165                 170                 175
Arg Thr Val Lys Ser Ile Arg Asp Ser Phe Thr Ser Gln Leu Glu Asn
            180                 185                 190
Ile Leu Cys Phe Phe Leu Val Tyr Arg Thr Thr Tyr Ser Phe Gly Val
        195                 200                 205
Cys Leu Met Lys Arg Phe Leu Phe Asn Lys Phe Phe Asn Arg His Pro
    210                 215                 220
Phe Thr Arg Val Lys Ser Cys Phe Ser Ser Ser Pro Ser Lys Phe
225                 230                 235                 240
Ser Phe Thr Gln Trp Leu Val Gly Phe Thr Asp Gly Asp Gly Cys Phe
                245                 250                 255
Ser Ile Ser Lys Gln Lys Met Lys Asn Gly Lys Asn Lys Trp Ser Thr
            260                 265                 270
Thr Phe Lys Leu Thr Gln Asn Thr Tyr Asn Tyr Arg Ile Leu Tyr Phe
        275                 280                 285
Ile Lys Arg Asn Leu Gly Ile Gly Ser Thr Tyr Lys Glu Ser Ser Thr
    290                 295                 300
Asn Thr Val Met Tyr Arg Leu Arg Arg Glu His Thr Lys Lys Ile
305                 310                 315                 320
Met Asp Ile Phe Asp Gln Phe Pro Leu Thr Lys Lys Tyr Trp Asp Tyr
                325                 330                 335
Tyr Leu Phe Lys Lys Ala Phe Leu Ile Leu Glu Asp Ala Asn Thr Asn
            340                 345                 350
Ser Phe Glu Lys Asn Ser Lys Thr Glu Glu Ile Arg Met Glu Lys Lys
        355                 360                 365
Ser Leu Lys Gln Tyr Ser Pro Val Asn Leu Glu Lys Tyr Leu Thr Lys
    370                 375                 380
Ser Trp Leu Ile Gly Phe Ile Glu Ala Glu Gly Ser Phe Tyr Leu Thr
385                 390                 395                 400
Gln Lys Ser Pro Val Arg Met Ile His Gly Phe Glu Ile Thr Gln Asn
                405                 410                 415
Tyr Glu Gln Pro Thr Thr Ala Gln Ile Ser Glu Phe Thr Phe Asn Ser
            420                 425                 430
Gln Ile Ser Pro Lys Met Lys Ser Lys Lys Asn Ser Leu Ile Thr Asn
        435                 440                 445
Tyr Ser Leu Ser Thr Ser Ser Lys Glu Arg Met Leu Phe Thr Ser Ser
    450                 455                 460
Tyr Phe Glu Asn Cys Phe Lys Gly Val Lys Ser Leu Glu Phe Lys Ile
465                 470                 475                 480
Trp Ser Arg Ser Leu Arg Lys Asn Tyr Asn Phe Glu Gln Thr Leu Arg
                485                 490                 495
Ala Arg Asp Leu Ile Arg Lys Leu Lys Asn Lys Tyr Ser Gly Ser Gln
            500                 505                 510
His Pro Lys Asp Lys
        515

<210> SEQ ID NO 12
```

```
<211> LENGTH: 304
<212> TYPE: PRT
<213> ORGANISM: Schizosaccharomyces pombe

<400> SEQUENCE: 12

Met Asn Lys Phe Phe Asn Arg His Pro Phe Thr Arg Val Lys Ser Cys
  1               5                  10                  15

Phe Ser Ser Ser Pro Ser Lys Phe Ser Phe Thr Gln Trp Leu Val
             20                  25                  30

Gly Phe Thr Asp Gly Asp Gly Cys Phe Ser Ile Ser Lys Gln Lys Met
             35                  40                  45

Lys Asn Gly Lys Asn Lys Trp Ser Thr Thr Phe Lys Leu Thr Gln Asn
 50                  55                  60

Thr Tyr Asn Tyr Arg Ile Leu Tyr Phe Ile Lys Arg Asn Leu Gly Ile
 65                  70                  75                  80

Gly Ser Thr Tyr Lys Glu Ser Ser Thr Asn Thr Val Met Tyr Arg Leu
                 85                  90                  95

Arg Arg Arg Glu His Thr Lys Lys Ile Met Asp Ile Phe Asp Gln Phe
                100                 105                 110

Pro Thr Leu Thr Lys Lys Tyr Trp Asp Tyr Tyr Leu Phe Lys Lys Ala
            115                 120                 125

Phe Leu Ile Leu Glu Asp Ala Asn Thr Asn Ser Phe Glu Lys Asn Ser
130                 135                 140

Lys Thr Glu Glu Ile Arg Met Glu Lys Lys Ser Leu Lys Gln Tyr Ser
145                 150                 155                 160

Pro Val Asn Leu Glu Lys Tyr Leu Thr Lys Ser Trp Leu Ile Gly Phe
                165                 170                 175

Ile Glu Ala Glu Gly Ser Phe Tyr Leu Thr Gln Lys Ser Pro Val Arg
            180                 185                 190

Met Ile His Gly Phe Glu Ile Thr Gln Asn Tyr Glu Gln Pro Thr Thr
            195                 200                 205

Ala Gln Ile Ser Glu Phe Thr Phe Asn Ser Gln Ile Ser Pro Lys Met
210                 215                 220

Lys Ser Lys Lys Asn Ser Leu Ile Thr Asn Tyr Ser Leu Ser Thr Ser
225                 230                 235                 240

Ser Lys Glu Arg Met Leu Phe Thr Ser Ser Tyr Phe Glu Asn Cys Phe
                245                 250                 255

Lys Gly Val Lys Ser Leu Glu Phe Lys Ile Trp Ser Arg Ser Leu Arg
            260                 265                 270

Lys Asn Tyr Asn Phe Glu Gln Thr Leu Arg Ala Arg Asp Leu Ile Arg
        275                 280                 285

Lys Leu Lys Asn Lys Tyr Ser Arg Gly Ser Gln His Pro Lys Asp Lys
290                 295                 300

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gccgcagaca aauuagucug                                                   20

<210> SEQ ID NO 14
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtggtggata tatccaccac                                              20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtggttggac ggtatatcca ccact                                        25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agtggtggat ataccgtcca accac                                        25

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Ala Gly Leu Ile Asp Ala Asp Gly
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 18

His His His His His His His His His His
1               5                   10
```